US011587670B2

(12) United States Patent
Nakano et al.

(10) Patent No.: US 11,587,670 B2
(45) Date of Patent: Feb. 21, 2023

(54) SURGERY SYSTEM, INFORMATION PROCESSING APPARATUS, AND INFORMATION PROCESSING METHOD

(71) Applicant: Sony Corporation, Tokyo (JP)

(72) Inventors: Takahito Nakano, Tokyo (JP); Takeshi Miyai, Kanagawa (JP); Keisuke Uyama, Kanagawa (JP); Daisuke Tsuru, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 325 days.

(21) Appl. No.: 16/762,513

(22) PCT Filed: Nov. 8, 2018

(86) PCT No.: PCT/JP2018/041508
§ 371 (c)(1),
(2) Date: May 8, 2020

(87) PCT Pub. No.: WO2019/098120
PCT Pub. Date: May 23, 2019

(65) Prior Publication Data
US 2020/0279644 A1    Sep. 3, 2020

(30) Foreign Application Priority Data
Nov. 17, 2017   (JP) .............................. JP2017-221675

(51) Int. Cl.
*G16H 40/40*      (2018.01)
*A61B 34/00*      (2016.01)
(Continued)

(52) U.S. Cl.
CPC ........... *G16H 40/40* (2018.01); *A61B 1/0005* (2013.01); *A61B 1/00006* (2013.01);
(Continued)

(58) Field of Classification Search
CPC ............ A61B 1/00006; A61B 1/00009; A61B 1/0005; A61B 34/25; A61B 90/361;
(Continued)

(56) References Cited

U.S. PATENT DOCUMENTS 7,366,934 B1\*  4/2008  Narayan ................ G16H 40/63
                                                          713/400
11,314,846 B1\*  4/2022  Colin ..................... G16H 40/40
(Continued)

FOREIGN PATENT DOCUMENTS

EP    0804031 A2   10/1997
EP    2945407 A1   11/2015
(Continued)

OTHER PUBLICATIONS

International Search Report and Written Opinion dated Feb. 20, 2019 for PCT/JP2018/041508 filed on Nov. 8, 2018, 12 pages.

*Primary Examiner* — Peter D Le
(74) *Attorney, Agent, or Firm* — Xsensus LLP

(57) ABSTRACT

A medical operation system includes an information processing apparatus, including processing circuitry configured to cause a map of an operating room to be displayed on a display, the map including an icon representing a device located in the operating room or accessible from the operating room, receive, via a user operation on the displayed map, designation information representing a designation of a change in at least one of an input source, an output destination, or an internal setting for the device, generate a control signal to control the device based on the designation information, and transmit the generated control signal to the device.

17 Claims, 36 Drawing Sheets

(51) Int. Cl.
*A61B 90/00* (2016.01)
*G16H 40/20* (2018.01)
*G16H 30/40* (2018.01)
*G16H 40/63* (2018.01)
*A61B 1/00* (2006.01)

(52) U.S. Cl.
CPC ........ *A61B 1/000094* (2022.02); *A61B 34/25* (2016.02); *A61B 90/361* (2016.02); *G16H 30/40* (2018.01); *G16H 40/20* (2018.01); *G16H 40/63* (2018.01)

(58) Field of Classification Search
CPC ........ G16H 30/40; G16H 40/20; G16H 40/40; G16H 40/63; G16H 10/00; G16H 15/00; G16H 20/00; G16H 30/00; G16H 40/00; G16H 50/00; G16H 70/00; G16H 80/00
See application file for complete search history.

(56) References Cited

U.S. PATENT DOCUMENTS

| | | |
|---|---|---|
| 2006/0004605 A1 | 1/2006 | Donoghue et al. |
| 2007/0268280 A1* | 11/2007 | Fujita ................ A61B 1/00045 345/204 |
| 2009/0282350 A1* | 11/2009 | Kawasaki .......... H04N 21/4135 715/764 |
| 2014/0135648 A1* | 5/2014 | Holoien ................ A61B 34/25 600/102 |
| 2014/0336824 A1 | 11/2014 | Sasaki et al. |
| 2015/0317068 A1* | 11/2015 | Marka .................. G06F 3/0488 715/835 |
| 2016/0381767 A1* | 12/2016 | Tiberi ................ G06F 3/04886 715/736 |

FOREIGN PATENT DOCUMENTS

| | | |
|---|---|---|
| EP | 3042548 A1 | 7/2016 |
| EP | 3048790 A1 | 7/2016 |
| EP | 3101905 A1 | 12/2016 |
| JP | 2001-112775 A | 4/2001 |
| JP | 2003-190181 A | 7/2003 |
| JP | 2005-535395 A | 11/2005 |
| JP | 2007-7041 A | 1/2007 |
| JP | 2013-236757 A | 11/2013 |
| JP | 2016-512073 A | 4/2016 |
| JP | 2017-504151 A | 2/2017 |
| WO | 2016/158000 A1 | 10/2016 |
| WO | 2017/094363 A1 | 6/2017 |

\* cited by examiner

SURGERY SYSTEM, INFORMATION PROCESSING APPARATUS, AND INFORMATION PROCESSING METHOD

CROSS-REFERENCE TO RELATED APPLICATIONS

This application is based on PCT filing PCT/JP2018/041508, filed Nov. 8, 2018, which claims the benefit of Japanese Priority Patent Application JP 2017-221675 filed Nov. 17, 2017, the entire contents of each are incorporated herein by reference.

TECHNICAL FIELD

The present disclosure relates to a surgery system, an information processing apparatus, and an information processing method.

BACKGROUND ART

In recent years, various kinds of devices are used on medical fronts. For example, devices such as a camera including an endoscope apparatus or the like, a recorder, a monitor, and a light are installed in a surgery room, and surgery is performed by using such devices.

There are systems for integrally controlling such devices. Such a system also provides a graphical user interface (GUI) for facilitating operation for controlling devices. For example, PTL 1 listed below discloses a surgery system including a control apparatus that is connected to a plurality of medical devices. In the surgery system, icons corresponding to the medical devices are displayed at predetermined intervals, and an operation screen of a medical device corresponding to a displayed icon is displayed in the case where the icon is operated.

CITATION LIST

Patent Literature

PTL 1: JP 2003-190181A

SUMMARY

Technical Problem

However, sometimes it is difficult to carry out control regarding a desired device by using the GUI provided in the above-described system. For example, in the case where a plurality of devices of the same type are installed in a surgery room, it is difficult to recognize correspondence between information (such as icons) indicating devices on the GUI and the devices that are actually installed. Therefore, it is difficult to select and control a desired device.

Accordingly, the present disclosure proposes a novel and improved surgery system, information processing apparatus, and information processing method that are capable of controlling a target device more easily.

Solution to Problem

According to an embodiment of the present disclosure, there is provided a medical operation system, comprising an information processing apparatus, including processing circuitry configured to (1) cause a map of an operating room to be displayed on a display, the map including an icon representing a device located in the operating room or accessible from the operating room, (2) receive, via a user operation on the displayed map, designation information representing a designation of a change in at least one of an input source, an output destination, and an internal setting for the device, (3) generate a control signal to control the device based on the designation information, and (4) cause the generated control signal to be transmitted to the device.

In addition, according to an embodiment of the present disclosure, there is provided a method of controlling a device located in a medical operating room and accessible during a medical procedure in the medical operating room, the method comprising: (1) displaying a map of the medical operating room, the map including an icon representing the device; (2) receiving, via a user operation on the displayed map, a designation of a change in one of an input source, an output destination, and an internal setting for the device; (3) generating a control signal to control the designated change, based on the received user operation; and (4) causing the generated control signal to be transmitted to the device.

In addition, according to an embodiment of the present disclosure, there is provided an image processing apparatus, comprising processing circuitry configured to (1) display a map of an operating room, the map including an icon representing a device located in the operating room or useable during a medical procedure in the medical operating room, (2) receive, via a user operation on the displayed map, a designation of a change in one of an input source, an output destination, and an internal setting for the device, and (3) generate a control signal to control the designated change, based on the received user operation; and a transmitter configured to transmit, to the device, the generated control signal.

Advantageous Effects of Invention

As described above, according to the embodiment of the present disclosure, it is possible to control a target device more easily.

Note that the effects described above are not necessarily limitative. With or in the place of the above effects, there may be achieved any one of the effects described in this specification or other effects that may be grasped from this specification.

DESCRIPTION OF EMBODIMENTS

Hereinafter, (a) preferred embodiment(s) of the present disclosure will be described in detail with reference to the appended drawings. Note that, in this specification and the appended drawings, structural elements that have substantially the same function and structure are denoted with the same reference sign, and repeated explanation of these structural elements is omitted.

Note that, the description is given in the following order.
<<1. Overview>>
<<2. Configuration of information processing apparatus>>
<<3. Operation>>
<<4. Specific example>>
<<5. Hardware configuration example>>
<<6. Conclusion>>

1. Overview

First, with reference to FIG. 1, a surgery system according to an embodiment of the present disclosure will be described.

Figure 1:
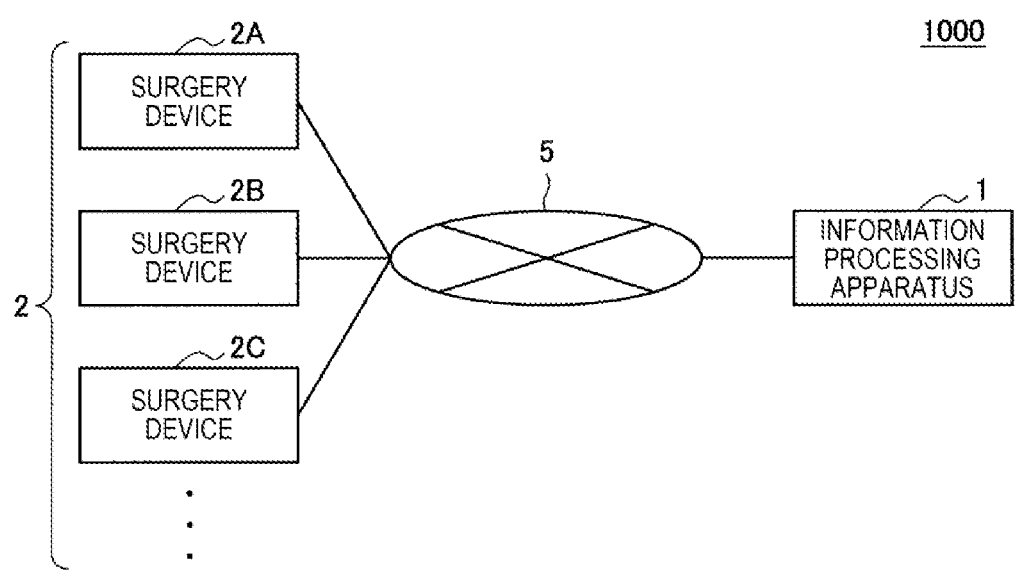
FIG. 1 is a diagram illustrating a schematic configuration of a surgery system 1000 according to an embodiment of the present disclosure.

FIG. 1 is a diagram illustrating a schematic configuration of a surgery system 1000 according to an embodiment of the present disclosure. As illustrated in FIG. 1, the surgery system 1000 according to the present embodiment includes an information processing apparatus 1, a plurality of surgery devices 2, and a network 5.

The information processing apparatus 1 is connected to the plurality of surgery devices 2 via the network 5 as illustrated in FIG. 1. The information processing apparatus 1 is an information processing apparatus for integrally handling and controlling the plurality of surgery devices 2. For example, the information processing apparatus 1 may be a personal computer (PC) or a tablet terminal. Note that, a detailed functional configuration of the information processing apparatus 1 will be described later with reference to FIG. 2.

The surgery devices 2 may be devices present in or outside of a surgery room. The surgery devices 2 may be used during surgery. Note that, although FIG. 1 illustrates three surgery devices 2A to 2C as the surgery devices 2, the number of surgery devices 2 is not specifically limited.

In the surgery room, there may be various devices that are to be used during surgery. In addition, it is also considered that a device installed outside of the surgery room is used during surgery. For example, it is considered that a recorder that stores an image captured in advance is installed in a room other than the surgery room, and the image stored in the recorder is seen during surgery by using a monitor installed in the surgery room. Note that, in the present specification, the image is not limited to a still image. The word "image" is used as an expression including a moving image.

In the present specification, the wording "surgery devices" is a generic term including devices that are present in or outside of a surgery room and that may be used during surgery. The surgery devices 2 illustrated in FIG. 1 may include a surgery device present in a surgery room and a surgery device present outside of the surgery room. The surgery device present outside of the surgery room is a device located accessible from the surgery room.

For example, the surgery devices 2 may include a camera (imaging apparatus), a recorder (storage apparatus), a monitor (display apparatus), a light, and various other devices that may be used during surgery.

The camera that is an example of the surgery devices 2 is a transmission device having a function (example of transmission function) of capturing an image and transmitting the image to other surgery devices 2 and the information processing apparatus 1. Note that, the surgery devices 2 may include a ceiling camera that is installed on a ceiling in a surgery room to capture situations in the whole surgery room, a surgical field camera that is installed on the ceiling in the surgery room to capture a place near hands of a surgeon, and a camera such as an endoscope or a microscope for observing an inside of a body cavity of a patient, for example.

The recorder that is an example of the surgery devices 2 stores images captured by the cameras during surgery, images captured in advance, or the like. For example, the recorder that is an example of the surgery devices 2 may store a computed tomography (CT) image captured during an examination carried out before surgery. In addition, the recorder that is an example of the surgery devices 2 is a transmission/reception device having a function (example of reception function) of receiving images from other surgery devices 2 and a function (example of transmission function) of transmitting images to other surgery devices 2 and the information processing apparatus 1.

The monitor that is an example of the surgery devices 2 displays an image captured by the camera during surgery, an image stored in the recorder, or the like. In addition, the monitor that is an example of the surgery devices 2 is a reception device having a function (example of reception function) of receiving images from other surgery devices 2. In addition, the monitor that is an example of the surgery devices 2 may also have a function of dividing a display area and simultaneously displaying a plurality of images.

The network 5 is a wired or wireless communication path through which information is transmitted from devices connected to the network 5. For example, the network 5 may be a local area network (LAN) or the like established in a hospital including the insides and outsides of surgery rooms. Note that, the network 5 is not limited thereto. The network 5 may include a public network such as the Internet, a telephone network, and a satellite communication network, various LANs including Ethernet (registered trademark), a wide area network (WAN), and the like. In addition, the network 5 may include a dedicated network such as an internet protocol-virtual private network (IP-VPN). In addition, although FIG. 1 illustrates the example in which the information processing apparatus 1 and the surgery devices 2 are connected via the network 5, one or all of the surgery devices 2 may be directly connected to the information processing apparatus 1.

In the surgery system 1000 according to the embodiment, it is possible for a user to integrally handle the plurality of surgery devices 2 by using the information processing apparatus 1. The information processing apparatus 1 has a function of carrying out control regarding the surgery devices 2, and provides a GUI for operating the surgery devices 2. Detailed configuration of the information processing apparatus 1 will be described later.

For example, the information processing apparatus 1 according to the present embodiment may display a layout screen that shows arrangement of the surgery devices 2, and receive user operation performed on the layout screen. The layout screen is a map of an operating room (a surgery room). The user operations provide designation information representing a designation of a change in at least one of an input source, an output destination, and an internal setting for the device. Such user operations that provide the designation information will be described in more detail below. In addition, the information processing apparatus 1 may carry out control regarding the surgery devices 2 on the basis of user operation performed on the layout screen. The arrangement of the surgery devices 2 may be changed in accordance with contents and procedures of surgery. According to such a configuration, the user is capable of intuitively operating a desired surgery device 2. In addition, according to such a configuration, the user is capable of distinguishing a plurality of surgery devices 2 and operating a desired surgery device 2 even in the case where the surgery system 1000 includes the plurality of surgery devices 2 of the same type.

The overview of the surgery system 1000 according to the present embodiment has been described above. Next, a detailed configuration of the information processing apparatus 1 for achieving the above-described effects will be described.

2. Configuration of Information Processing Apparatus

Figure 2:
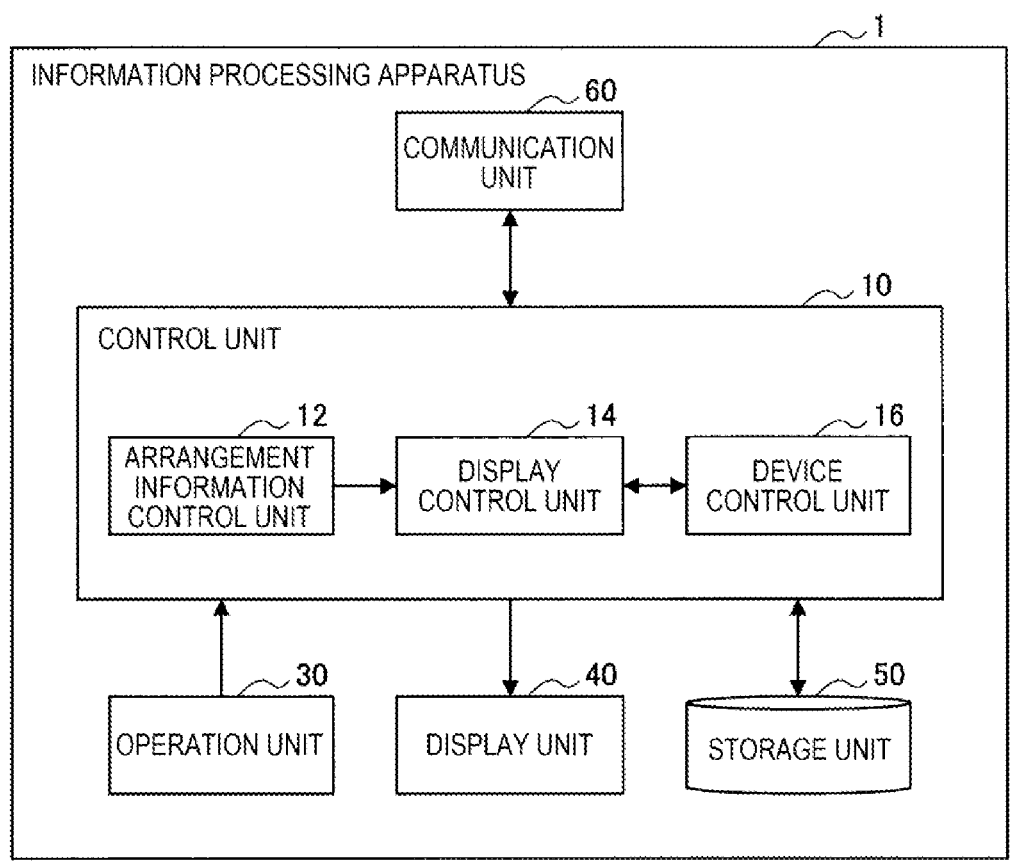
FIG. 2 is a block diagram illustrating a configuration example of an information processing apparatus 1 according to the embodiment.

FIG. 2 is a block diagram illustrating a configuration example of the information processing apparatus 1 according to the present embodiment. As illustrated in FIG. 2, the information processing apparatus 1 includes a control unit 10, an operation unit 30, a display unit 40, a storage unit 50, and a communication unit 60. Note that, hereinafter, an overall configuration of the information processing apparatus 1 will be described first, and then a detailed configuration of the control unit 10 will be described.

2-1. Apparatus Configuration (Control Unit)

The control unit 10 functions as an arithmetic processing apparatus and a control apparatus to control entire operation in the information processing apparatus 1 in accordance with various kinds of programs. In addition, the control unit 10 according to the embodiment functions as an arrangement information control unit 12, a display control unit 14, and a device control unit 16 as illustrated in FIG. 2. Note that, functions of the control unit 10 as the arrangement information control unit 12, the display control unit 14, and the device control unit 16 will be described later.

(Operation Unit)

The operation unit 30 receives operation performed by a user (user operation). For example, the operation unit 30 according to the present embodiment receives user operation performed on various kinds of screens that the display control unit 14 (to be described later) causes the display unit 40 to display. For example, the operation unit 30 may be implemented by a mouse, a keyboard, a touchscreen, a button, a switch, a lever, a dial, or the like.

(Display Unit)

The display unit 40 displays various kinds of screens under the control of the display control unit 14 (to be described later). Note that, although the operation unit 30 and the display unit 40 are illustrated as separate structural elements in the example illustrated in FIG. 2, the information processing apparatus 1 may include a touchscreen display having the functions of the operation unit 30 and the functions of the display unit 40.

(Storage Unit)

The storage unit 50 stores data such as programs and parameters to be used by the control unit 10 executing the above-described functions. The storage unit 50 may store data for the display control unit 14 to cause the various kinds of screens to be displayed. For example, the storage unit 50 may store arrangement information regarding arrangement of the surgery devices 2, information regarding functions of the surgery devices 2, various kinds of icons, and the like.

(Communication Unit)

The communication unit 60 is a communication interface that mediates communication between the information processing apparatus 1 and other apparatuses. The communication unit 60 supports any wireless or wired communication protocol, and directly establishes communication connection with the other apparatuses or establishes communication connection with the other apparatuses via the network 5 described above with reference to FIG. 1, for example. For example, the communication unit 60 may transmit control signals generated by the device control unit 16 (to be described later) to surgery devices 2. In addition, the communication unit 60 may receive, from the surgery devices 2, information regarding statuses of the surgery devices 2, information acquired by the surgery devices 2 (such as images that are being captured), information stored in the surgery devices 2 (such as images captured in advance), and the like.

2-2. Configuration of Control Unit

The overall configuration example of the information processing apparatus 1 has been described above. Next, details of the functions of the control unit 10 as the arrangement information control unit 12, the display control unit 14, and the device control unit 16 will be described.

(Arrangement Information Control Unit)

The arrangement information control unit 12 provides arrangement information related to arrangement of the surgery devices 2 to the display control unit 14. The arrangement information may include information of positions, attitudes, and the like of the surgery devices 2, for example. Note that, the information of the position of the surgery device 2 may include information indicating in which room the surgery device 2 is present, and may further include information indicating at which position in the room the surgery device 2 is present.

For example, the arrangement information control unit 12 may generate arrangement information on the basis of user operation received through the operation unit 30.

Alternatively, the arrangement information control unit 12 may automatically generate the arrangement information. For example, the arrangement information control unit 12 may recognize positions and attitudes of respective surgery devices 2 among the surgery devices 2 and generate the arrangement information on the basis of an image received from a camera (such as the surgical field camera or the like) installed at a higher perspective position. In addition, in the case where beacons are connected to the surgery devices 2 for recognizing their positions, the arrangement information control unit 12 may generate arrangement information on the basis of the beacons.

In addition, the arrangement information control unit 12 may cause the storage unit 50 to store the generated arrangement information. Subsequently, the arrangement information control unit 12 may select a piece of arrangement information corresponding to current arrangement of the surgery devices 2 from a plurality of pieces of arrangement information that have been generated in advance and that are stored in the storage unit 50. For example, such selection may be carried out on the basis of user operation. For example, the selection may be carried out in accordance with arrangement instructions corresponding to respective procedures or respective doctors. This configuration enables reduction in load related to generation of arrangement information.

Note that, although the example in which arrangement information is generated by the arrangement information control unit 12 in the information processing apparatus 1 has been described above, arrangement information may be generated by another apparatus. In such a case, the arrangement information control unit 12 may provide the display control unit 14 with arrangement information received by the communication unit 60 from the another apparatus.

(Display Control Unit)

The display control unit 14 causes the display unit 40 to display various kinds of screens. Note that, in the present specification, the wording "screen" means one display set displayed on the display unit 40. The display control unit 14 may cause the display unit 40 to simultaneously display a plurality of images. In addition, one screen may include another screen.

Figure 3:
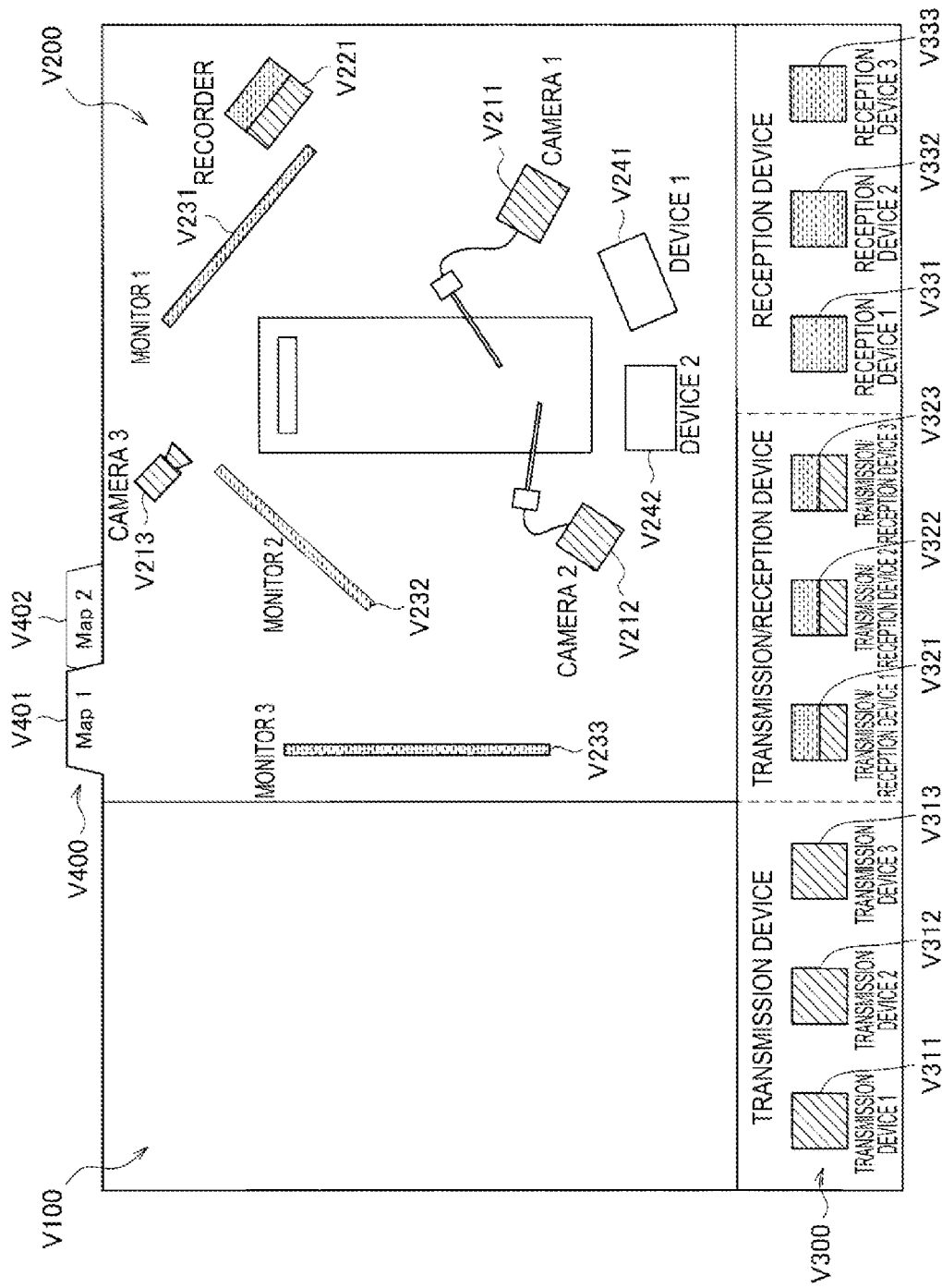
FIG. 3 is an explanatory diagram illustrating an example of a screen that a display control unit 14 causes a display unit 40 to display.

FIG. 3 is an explanatory diagram illustrating an example of the screen that the display control unit 14 causes the display unit 40 to display. In the example illustrated in FIG. 3, the display unit 40 is divided into four display areas including a display area V100, a display area V200, a display area V300, and a display area V400.

In the example illustrated in FIG. 3, the display area V100 displays nothing. The display control unit 14 may cause various kinds of screens to be displayed in the display area V100 on the basis of user operation performed on a screen displayed in another display area.

For example, it is possible for the display control unit 14 to cause a setting screen to be displayed in the display area V100 on the basis of user operation performed on a layout screen (to be described later) displayed in the display area V200. The setting screen is used for configuring settings of a surgery device 2. A specific example of such display control will be described later with reference to FIG. 9 to FIG. 12 and the like.

In addition, it is possible for the display control unit 14 to cause a preview screen to be displayed on the basis of user operation performed on the layout screen (to be described later) displayed in the display area V200 or a device list screen (to be described later) displayed in the display area V300. The preview screen includes an image transmitted from a surgery device 2. A specific example of such display control will be described later with reference to FIG. 14 to FIG. 23 and the like.

In addition, in the example illustrated in FIG. 3, the display control unit 14 causes a layout screen to be displayed in the display area V200. The layout screen shows arrangement of surgery devices 2 present in a surgery room. For example, the display control unit 14 may cause the layout screen to be displayed on the basis of arrangement information acquired from the arrangement information control unit 12. Note that, it is only necessary for the layout screen that the display control unit 14 causes to be displayed, to be a screen showing arrangement of at least one of the plurality of surgery devices 2 connected to the information processing apparatus 1.

As illustrated in FIG. 3, the display control unit 14 may cause icons V211 to V213, V221, V231 to V233, and V241 to V242 that correspond to surgery devices 2 to be displayed in the layout screen. Note that, as illustrated in FIG. 3, the display control unit 14 may cause respective texts to be displayed near the icons. The respective texts indicate types of the surgery devices 2 corresponding to the icons. As illustrated in FIG. 3, the icons V211 to V213 are icons corresponding to respective cameras that are examples of the surgery devices 2. In addition, the icon V221 is an icon corresponding to a recorder that is an example of the surgery devices 2. In addition, the icons V231 to V233 are icons corresponding to respective monitors that are examples of the surgery devices 2. In addition, the icons V241 to V242 are icons corresponding to other types of respective surgery devices 2.

In addition, the display control unit 14 may cause the icons corresponding to the surgery devices 2 to be displayed on the basis of positions and attitudes of the surgery devices 2 in a real space (in the surgery room in the example illustrated in FIG. 3). In the example illustrated in FIG. 3, the display control unit 14 causes the icons corresponding to the surgery devices 2 to be displayed at positions in the layout screen in accordance with positions of the surgery devices 2 in the real space. In addition, in the example illustrated in FIG. 3, the display control unit 14 causes the icons corresponding to the surgery devices 2 to be displayed with attitudes in the layout screen in accordance with attitudes (such as angles) of the surgery devices 2 in the real space. By using such a layout screen as illustrated in FIG. 3, a user is capable of easily recognizing correspondence between the surgery devices 2 and icons even in the case where there are a plurality of surgery devices 2 (such as cameras or monitors) of the same type, for example.

In addition, in the example illustrated in FIG. 3, the display control unit 14 causes the device list screen to be displayed in the display area V300. The device list screen includes icons V311 to V313, V321 to V323, and V331 to V333 corresponding to the surgery devices 2 present in or outside of the surgery room. Such a configuration enables the user to recognize surgery devices 2 present outside of the surgery room and operate the surgery devices 2 present outside of the surgery room. Note that, in the example illustrated in FIG. 3, icons corresponding to the surgery devices 2 present outside of the surgery room are displayed in the device list screen such that the icons are classified by functions of the surgery devices 2.

The display control unit 14 may display icons corresponding to surgery devices 2 on the basis of functions of the surgery devices 2. For example, the display control unit 14 may cause icons to be displayed such that the icons are displayed with colors, patterns, or shapes in accordance with functions of surgery devices 2 corresponding to the respective icons. Such a configuration enables the user to easily recognize the functions of the surgery devices 2 corresponding to the icons.

For example, the display control unit 14 may cause an icon to be displayed on the basis of whether or not a surgery device 2 has a transmission function of transmitting predetermined information (such as images) to other surgery devices 2. Alternatively, the display control unit 14 may cause an icon to be displayed on the basis of whether or not a surgery device 2 has a reception function of receiving predetermined information (such as images) from other surgery devices 2.

In the example illustrated in FIG. 3, icons corresponding to surgery devices 2 having the transmission function of transmitting images, icons corresponding to surgery devices 2 having the reception function of receiving images, and icons corresponding to surgery devices 2 having both the transmission function and the reception function are displayed in a distinguishable manner. Specifically, in the example illustrated in FIG. 3, a hatch pattern of the icons V211 to V213 and V311 to V313 indicates that the respective icons correspond to surgery devices 2 having the transmission function of transmitting images. In addition, in the example illustrated in FIG. 3, a hatch pattern of the icons V221 and V321 to V323 indicates that the respective icons correspond to surgery devices 2 having both the transmission function of transmitting images and the reception function of receiving images. In addition, in the example illustrated in FIG. 3, a hatch pattern of the icons V231 to V233 and V331 to V333 indicates that the respective icons correspond to surgery devices 2 having the reception function of receiving images. Note that, in the example illustrated in FIG. 3, surgery devices 2 corresponding to icons V241 and V242 do not have any of the transmission function and the reception function.

As described later, the device control unit 16 controls connection between the surgery devices 2 having the transmission function and the surgery devices 2 having the reception function on the basis of user operation. Accordingly, display of the icons that help distinguishing whether or not the respective surgery devices 2 have the transmission function and the reception function, is convenient for the user.

In the example illustrated in FIG. 3, the display area V400 is placed above the display area V200. The display area V400 displays a tab V401 and a tab V402. The display control unit 14 may switch display related to a screen displayed in the display area V200 in accordance with user operation performed on the tab V401 or the tab V402. Note that, in the example illustrated in FIG. 3, the tab V401 is selected.

For example, the display control unit 14 may cause a plurality of layout screens to be displayed. The display control unit 14 may switch display of a layout screen to be displayed in the display area V200 in accordance with user operation performed on the tab V401 or the tab V402. In such a case, for example, a layout screen displayed in the display area V200 when the tab V401 is selected shows arrangement of surgery devices 2 differently from a layout screen displayed in the display area V200 when the tab V402 is selected. A specific example of such display control will be described later with reference to FIG. 24 to FIG. 25.

The examples of the screens and icons that the display control unit 14 causes the display unit 40 to display have been described above with reference to FIG. 3. However, the screens and icons caused to be displayed by the display control unit 14 are not limited to the example illustrated in FIG. 3. Specific examples of the above-described screens, the above-described icons, and other screens and icons that the display control unit 14 may cause the display unit 40 to display will be described later in detail with reference to FIG. 5 to FIG. 35.

(Device Control Unit)

The device control unit 16 generates control signals for carrying out control regarding the surgery devices 2. For example, the device control unit 16 may generate the control signals on the basis of user operation performed on various kinds of screens caused to be displayed by the display control unit 14.

The device control unit 16 may generate the control signals on the basis of user operation performed on the layout screen. For example, the device control unit 16 may generate a control signal for carrying out control regarding a surgery device 2 corresponding to an icon displayed on the layout screen in the case where user operation is performed on the icon. As described above, the layout screen shows arrangement of surgery devices 2. Therefore, the user is capable of easily recognizing correspondence between the surgery devices 2 and respective icons. Therefore, such a configuration enables a user to easily recognize an icon corresponding to a surgery device 2 that the user wants to control, and intuitively operate it.

In addition, the device control unit 16 may generate a control signal on the basis of user operation performed on a plurality of icons caused to be displayed by the display control unit 14. With regard to the plurality of icons, all of the icons may be included in the layout screen or the device list screen. Alternatively, the icons may be a combination of icons included in the layout screen and icons included in the device list screen.

For example, the device control unit 16 may generate a control signal for controlling connection between the plurality of surgery devices 2 (hereinafter, also referred to as inter-device connection) on the basis of user operation performed on the plurality of icons.

For example, the device control unit 16 may generate a control signal for controlling connection between a surgery device 2 having the function of transmitting images (hereinafter, also referred to as a first device) and a surgery device 2 having the function of receiving images (hereinafter, also referred to as a second device). For example, a control signal for controlling the connection between the first device and the second device may be generated on the basis of user operation performed on an icon corresponding to the first device and an icon corresponding to the second device. Note that, such a control signal may be transmitted to at least any one of the first device or the second device by using the communication unit 60, for example.

Note that, the control signal for controlling inter-device connection may be generated on the basis of other user operation. For example, the device control unit 16 may generate the control signal for controlling inter-device connection such that the first device transmits an image to the second device on the basis of user operation performed on the preview screen and the layout screen that are caused to be displayed by the display control unit 14. For example, it is also possible to generate the control signal for controlling inter-device connection such that the first device transmits an image to the second device on the basis of user operation performed on the preview screen including the image to be transmitted from the first device and the icon corresponding to the second device included in the layout screen. Such a configuration enables the user to see the image transmitted from the first device and perform operation regarding the inter-device connection between the first device and the second device.

In addition, the device control unit 16 may generate a control signal regarding settings of a surgery device 2 caused to be displayed by the display control unit 14, on the basis of user operation performed on a setting screen for configuring the settings of the surgery device 2. For example, the generated control signal is transmitted to the surgery device 2 by using the communication unit 60.

Note that, the control signals generated by the device control unit 16 are not limited thereto. A specific example regarding the above-described control signals and a specific example of other control performed by the device control unit 16 will be described later together with specific examples of display control with reference to FIG. 5 to FIG. 35.

3. Operation

Figure 4:
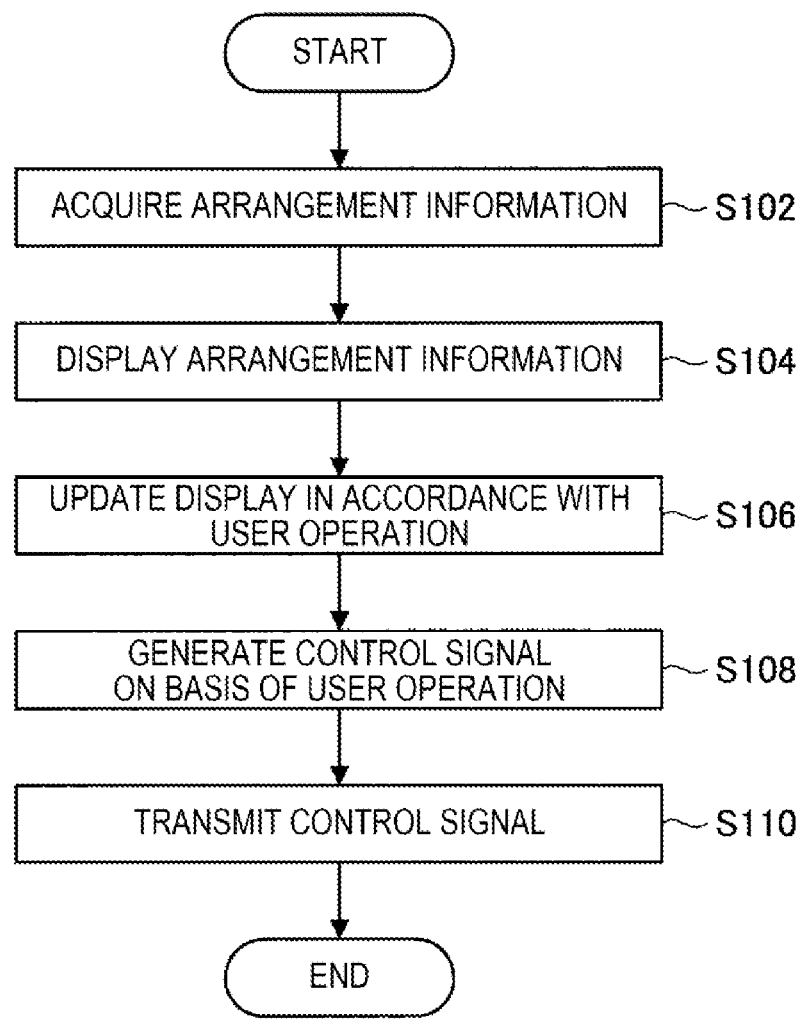
FIG. 4 is a flowchart illustrating an operation example of an information processing apparatus 1 according to the embodiment.

The configuration example of the information processing apparatus 1 according to the present embodiment has been described above. Next, with reference to FIG. 4, an operation example of the information processing apparatus 1 according to the present embodiment will be described. FIG. 4 is a flowchart illustrating the operation example of the information processing apparatus 1 according to the present embodiment.

First, as illustrated in FIG. 4, the display control unit 14 acquires arrangement information from the arrangement information control unit 12 (S102). Next, the display control unit 14 causes the display unit 40 to display a layout screen showing arrangement of surgery devices 2 on the basis of the arrangement information acquired in Step S102 (S104).

When the user operation is performed on the screen displayed on the display unit 40, the display control unit 14 controls the display such that the display is updated on the basis of the user operation (S106), and the device control unit 16 generates a control signal for controlling a surgery device 2 on the basis of the user operation (S108). Next, the communication unit 60 transmits the control signal generated in Step S108 to the surgery device 2 (S110).

The operation example of the information processing apparatus 1 according to the present embodiment has been described above. Note that, the example illustrated in FIG. 4 is a mere example. The operation of the information processing apparatus 1 is not limited thereto. Specifically, the processes in Step S106 to Step S110 in FIG. 4 may vary in accordance with user operation. For example, the processes in Step S106 and Step S108 may be performed only in the case where user operation is performed. One of the processes or both of the processes may be performed in accordance with user operation. In addition, the process in Step S110 may be performed in the case where the process in Step S108 is performed.

4. Specific Examples

The operation of the information processing apparatus 1 according to the present embodiment has been described above. Next, in the present embodiment, the screens and icons that are displayed by the display unit 40 under the control of the display control unit 14 and the user operation for causing the device control unit 16 to generate the control signal will be described in more detail with reference to FIG. 5 to FIG. 35.

Note that, in the following specific examples, examples in which user operation is performed using a mouse that is an example of the operation unit 30 will be mainly described. However, the present technology is not limited thereto. Various kinds of user operation may be appropriately designed in accordance with the form of the operation unit 30 of the information processing apparatus 1.

4-1. First Specific Example

First, an example in which user operation is performed on a layout screen regarding control of inter-device connection will be described as a first specific example with reference to FIG. 5 to FIG. 8. FIG. 5 to FIG. 8 are explanatory diagrams illustrating the first specific example according to the present embodiment.

Figure 5:
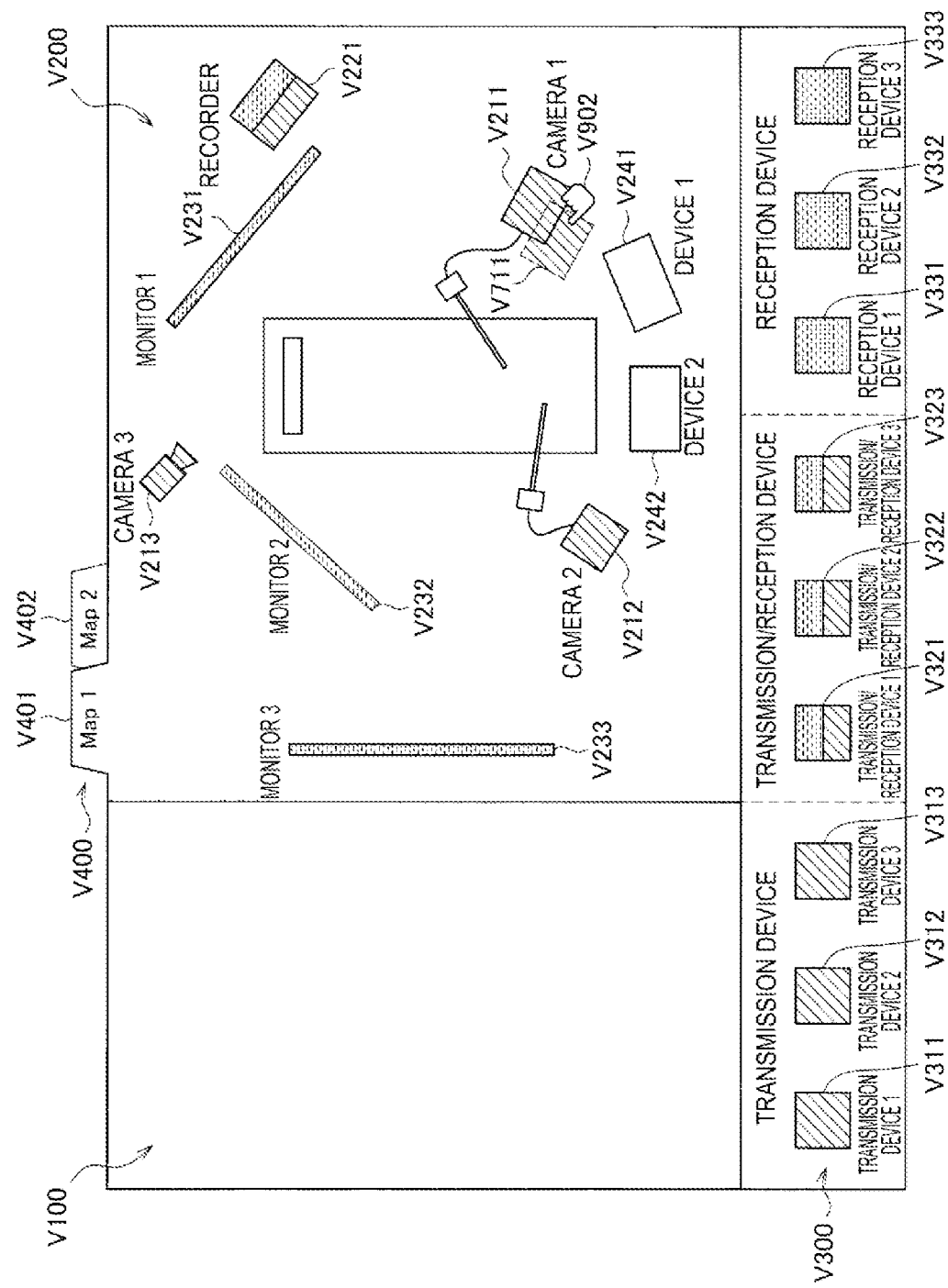
FIG. 5 is an explanatory diagram illustrating a first specific example according to the embodiment.

FIG. 5 illustrates a state in which drag operation (user operation for moving a mouse while pressing a button of the mouse) is performed on the icon V211 included in the layout screen by using a mouse cursor V902 in the state illustrated in FIG. 3. Here, as described above, the surgery device 2 corresponding to the icon V211 is a camera having the function of transmitting images. In this specific example, the surgery device 2 corresponding to the icon V211 may be referred to as a first device.

When the drag operation is performed on the icon V211 included in the layout screen as illustrated in FIG. 5, a drag icon (also referred to as a ghost) V711 corresponding to the icon V211 is displayed. The drag icon V711 is displayed such that the drag icon V711 follows movement of the mouse cursor V902 while performing the drag operation.

Figure 6:
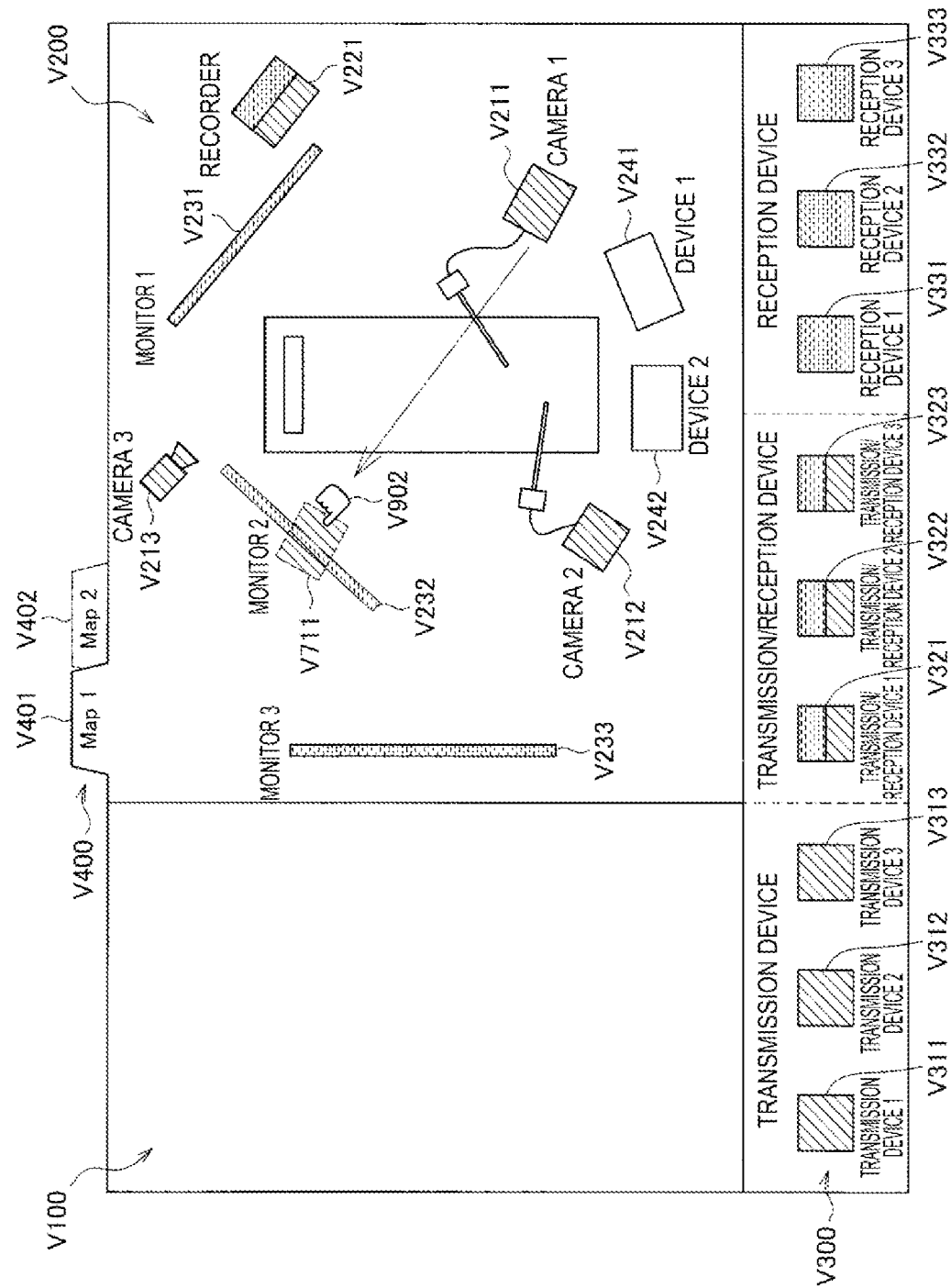
FIG. 6 is an explanatory diagram illustrating the first specific example according to the embodiment.

Next, FIG. 6 illustrates a state in which the mouse cursor V902 is moved in the state illustrated in FIG. 5 and drag operation is performed such that the drag icon V711 overlaps the icon V232. Here, as described above, the surgery device 2 corresponding to the icon V232 is a monitor having the function of receiving images. In this specific example, the surgery device 2 corresponding to the icon V232 may be referred to as a second device. In addition, in this specific example, the second device further has a function of dividing the display area and simultaneously displaying a plurality of images. More specifically, the second device is capable of dividing the display area into four areas and simultaneously displaying a maximum of four images.

Figure 7:
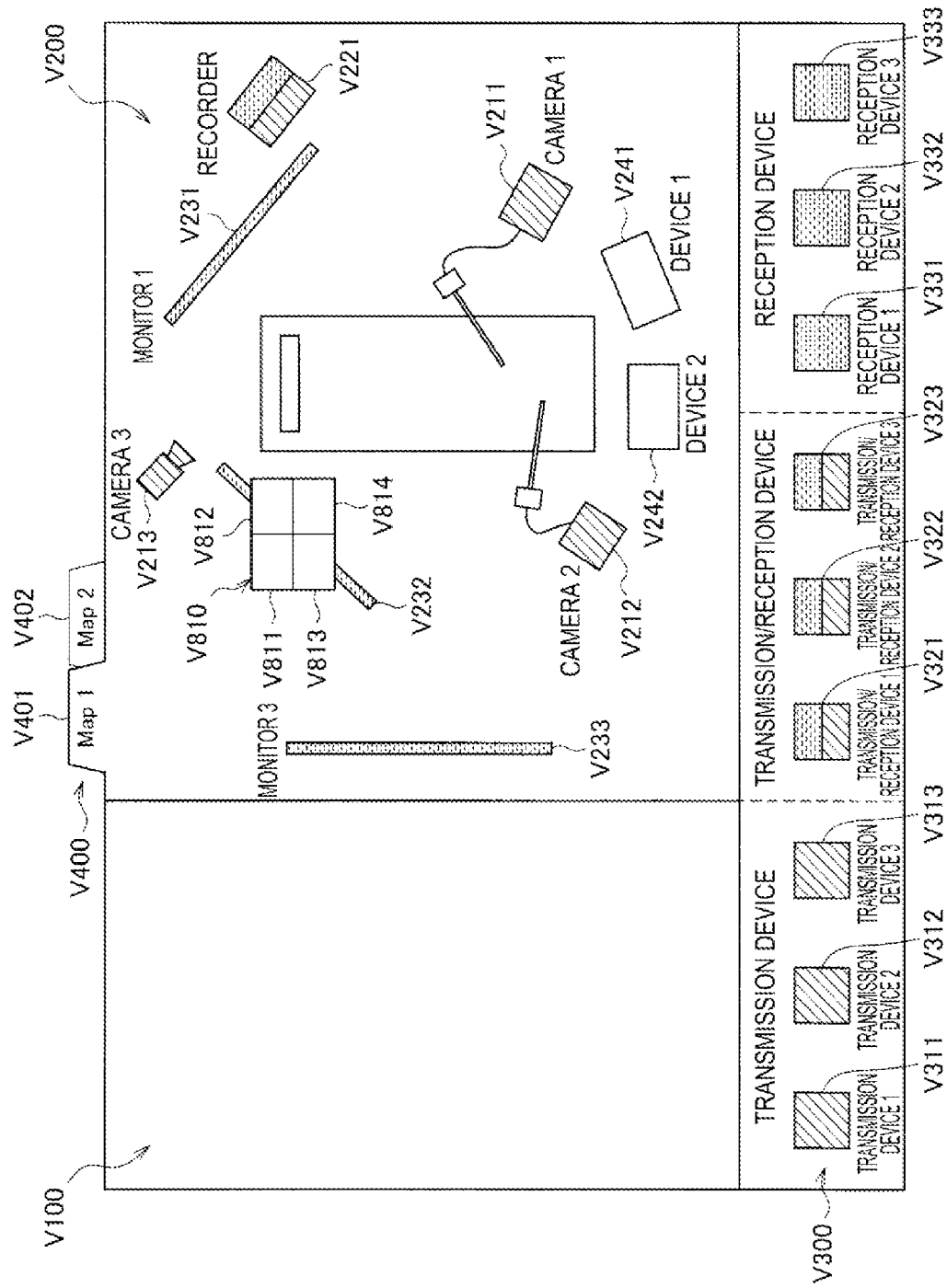
FIG. 7 is an explanatory diagram illustrating the first specific example according to the embodiment.

When drop operation (user operation for releasing the button of the mouse) is performed in the state illustrated in FIG. 6, the state transitions to a state illustrated in FIG. 7. In the state of FIG. 7, the display control unit 14 causes a display area selection screen V810 to be displayed. The display area selection screen V810 is a pop-up screen for selecting a display position of an image transmitted from the first device to the second device in the second device. The display area selection screen V810 includes display positions in the second device, in other words, divided area V811 to V814 corresponding to divided display areas.

Figure 8:
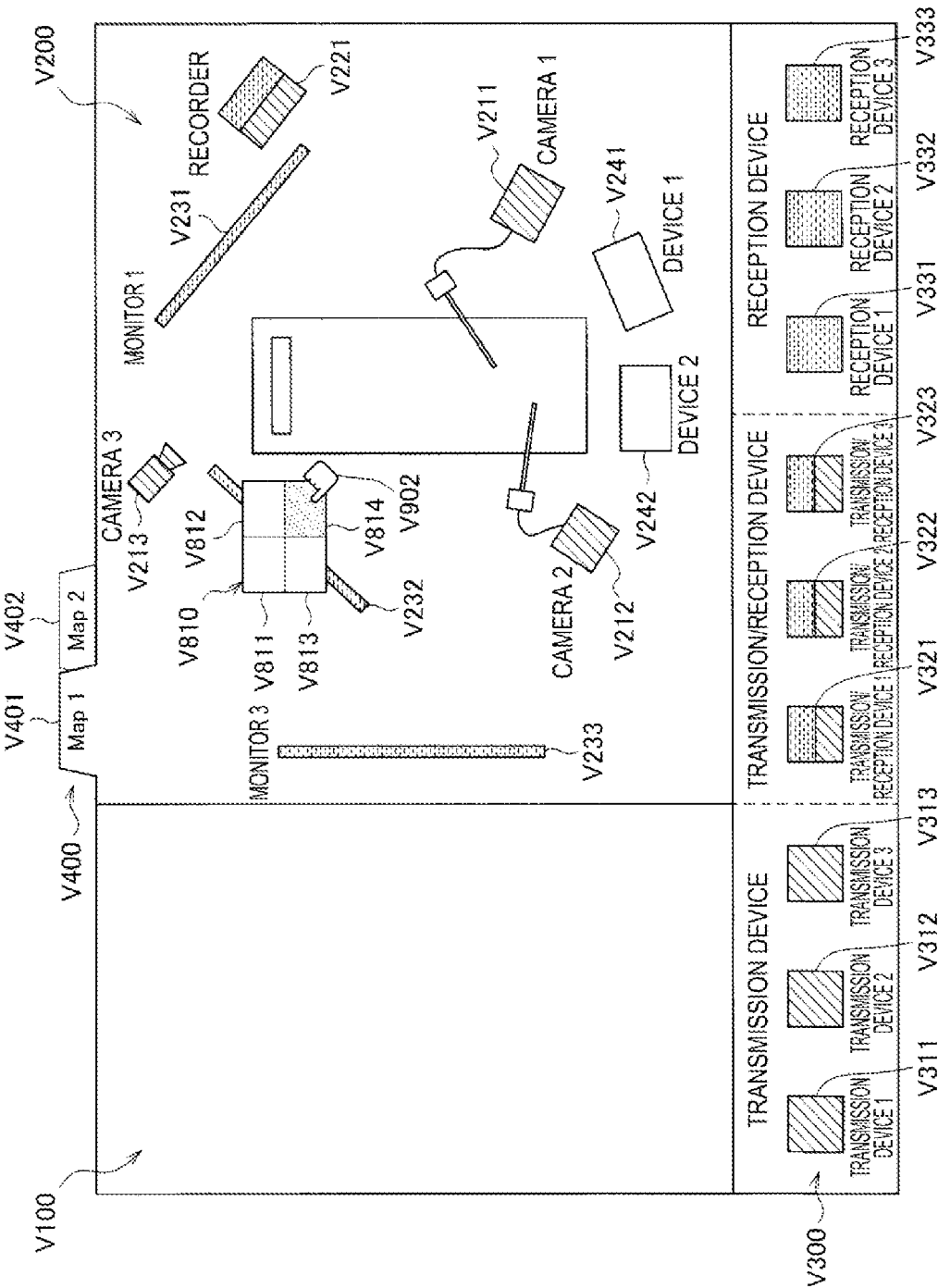
FIG. 8 is an explanatory diagram illustrating the first specific example according to the embodiment.

FIG. 8 illustrates a state in which selection operation (for example, user operation for pressing a button of the mouse at an appropriate mouse position) is performed on the divided area V814 included in the display area selection screen V810 in the state illustrated in FIG. 7. The device control unit 16 may generate a control signal for controlling inter-device connection such that the first device transmits an image to the second device, on the basis of the above-described series of user operation performed on the icon V211 corresponding to the first device and the icon V232 corresponding to the second device. Such a configuration enables the user to intuitively perform operation for the inter-device connection.

In addition, in the case where the above-described selection operation is performed on the display area selection screen V810, the device control unit 16 may generate a control signal for carrying out control regarding a display position in the second device on the basis of the selection operation. The control signal may be a control signal for designating a display position corresponding to the selection operation. Such a configuration enables the user to intuitively perform operation for designating a display position.

Note that, the example in which the second device has the function of dividing the display area and simultaneously displaying a plurality of images has been described above. However, in the case where the second device is a monitor for displaying an image on the entire display area, the device control unit 16 may generate a control signal for controlling the inter-device connection such that the first device transmits an image to the second device at a time when the drop operation is performed in the state illustrated in FIG. 6, for example.

4-2. Second Specific Example

Next, an example in which user operation is performed for carrying out control regarding settings of a surgery device 2 will be described as a second specific example with reference to FIG. 9 to FIG. 13. FIG. 9 to FIG. 13 are explanatory diagrams illustrating the second specific example according to the present embodiment.

Figure 9:
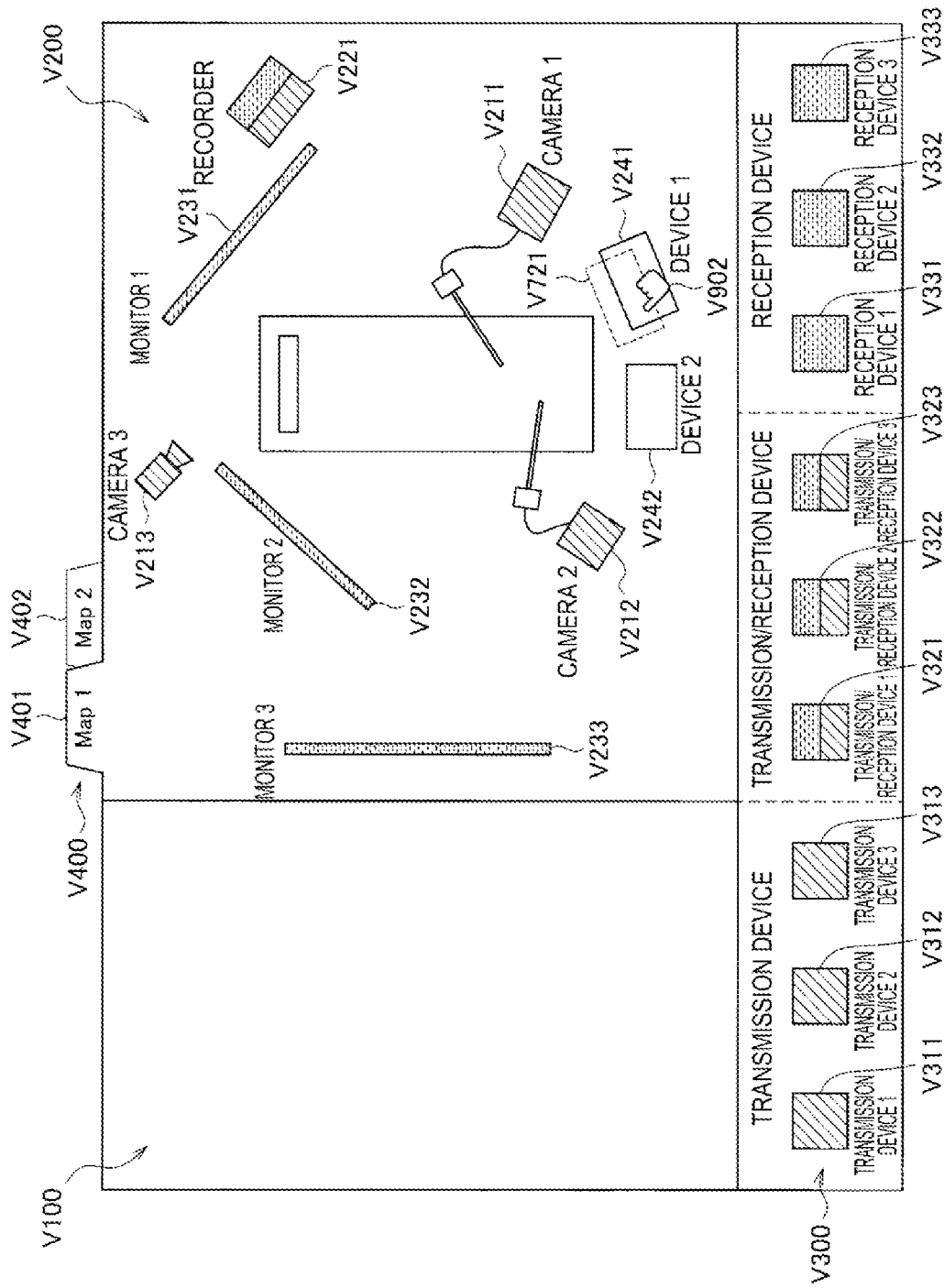
FIG. 9 is an explanatory diagram illustrating a second specific example according to the embodiment.

FIG. 9 illustrates a state in which drag operation is performed on the icon V241 included in the layout screen by using the mouse cursor V902 in the state illustrated in FIG. 3, and a drag icon V721 corresponding to the icon V241 is displayed.

Figure 10:
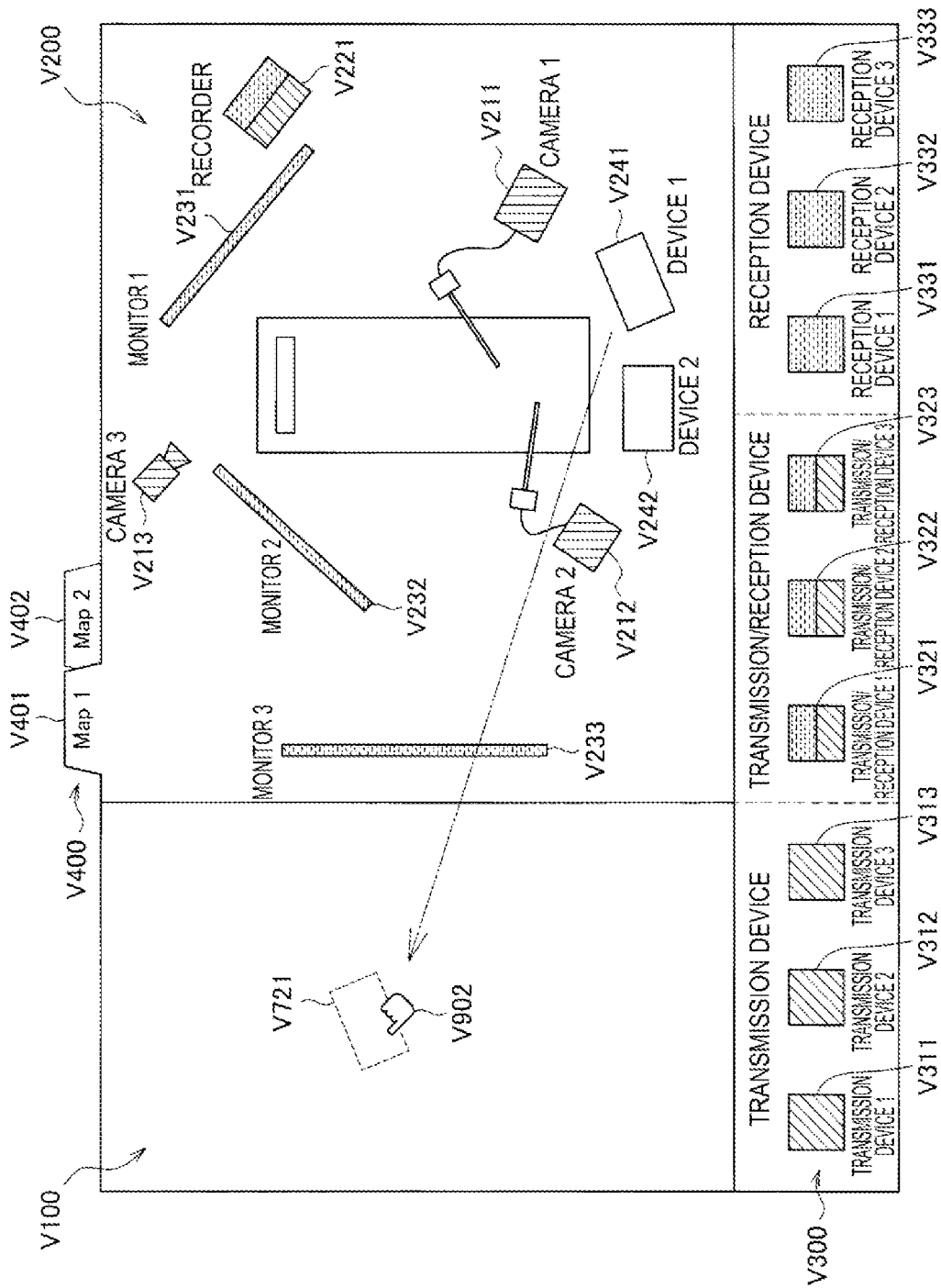
FIG. 10 is an explanatory diagram illustrating the second specific example according to the embodiment.

Next, FIG. 10 illustrates a state in which the mouse cursor V902 is moved in the state illustrated in FIG. 9 and drag operation is performed such that the drag icon V721 enters the display area V100. When the drop operation is performed in the state illustrated in FIG. 10, the state transitions to a state illustrated in FIG. 11. In the state illustrated in FIG. 11, the display control unit 14 causes a setting screen to be displayed in the display region V100. The setting screen is a setting screen of the surgery device 2 corresponding to the icon V241.

Figure 11:
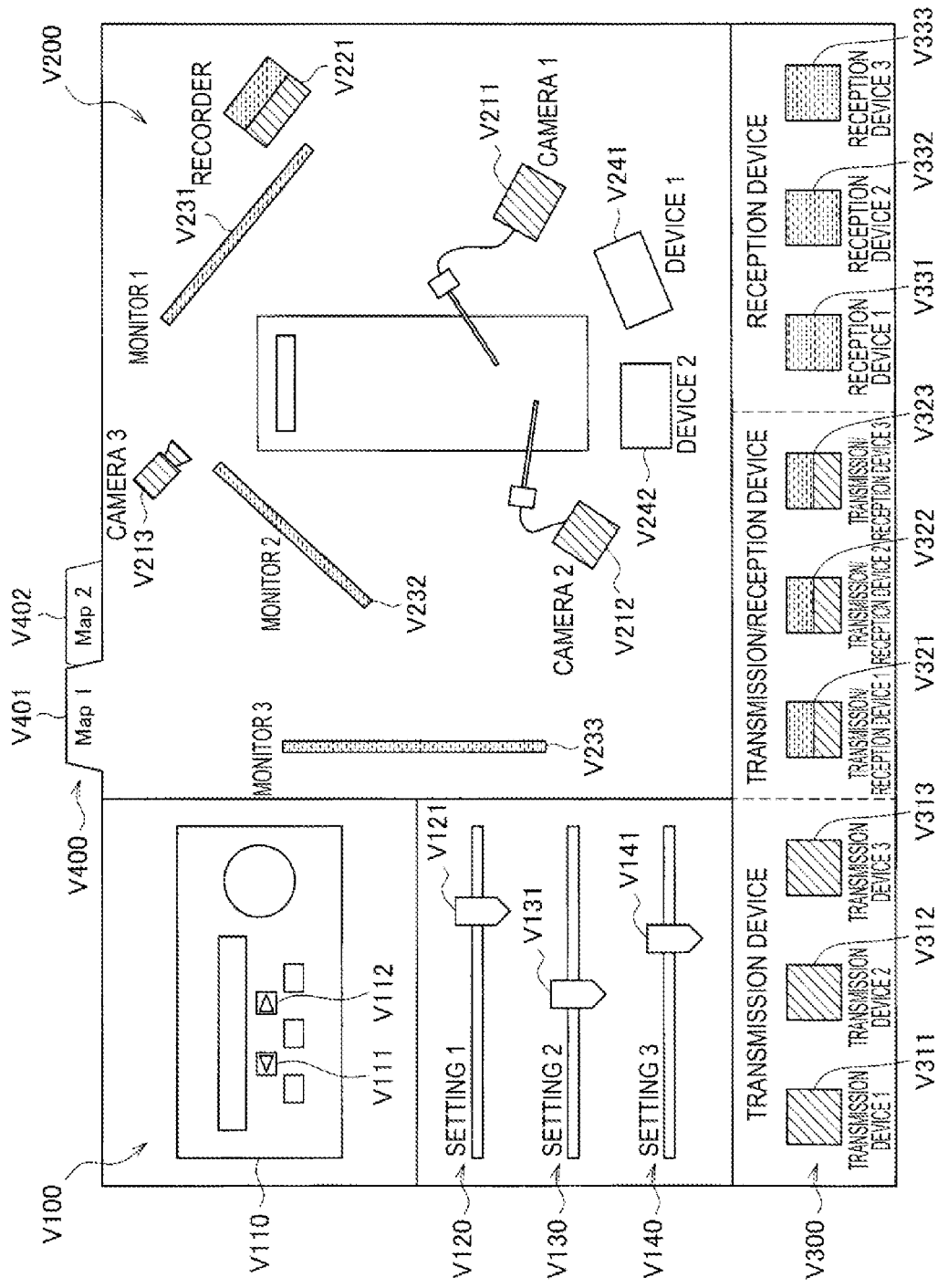
FIG. 11 is an explanatory diagram illustrating the second specific example according to the embodiment.

The icon V110 illustrated in FIG. 11 has appearance similar to an actual operation unit of the surgery device 2 corresponding to the icon V241. For example, in the case where the user performs selection operation on a button V111, a button V112, or the like, the device control unit 16 may generate a control signal for carrying out control regarding a setting of the surgery device 2 corresponding to the icon V241 in accordance with the selection operation. Such a configuration enables the user to perform operation regarding settings by using the setting screen as if the user has directly touched the actual surgery device 2 and performed the operation regarding settings.

Figure 12:
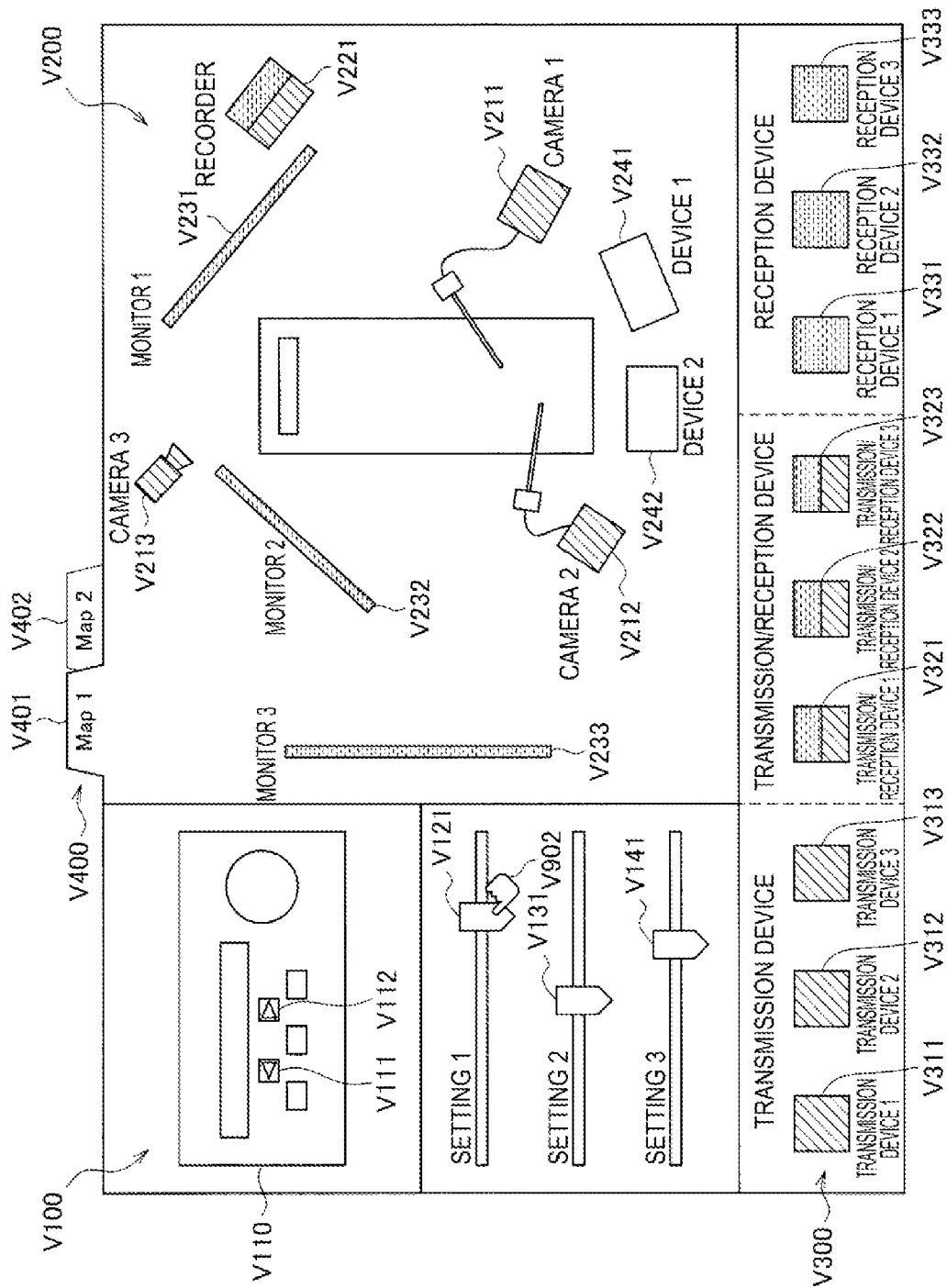
FIG. 12 is an explanatory diagram illustrating the second specific example according to the embodiment.

In addition, as illustrated in FIG. 11, the setting screen displayed in the display area V100 includes setting interfaces V120, V130, and V140 for configuring settings of the surgery device 2 corresponding to the icon V241. In addition, the setting interfaces V120, V130, and V140 respectively include sliders V121, V131, and V141. For example, as illustrated in FIG. 12, the user is capable of using the mouse cursor V902 to perform drag operation on the slider V121. In addition, on the basis of the drag operation, the device control unit 16 may generate a control signal for carrying out control regarding settings associated with the setting interface V120.

Figure 13:
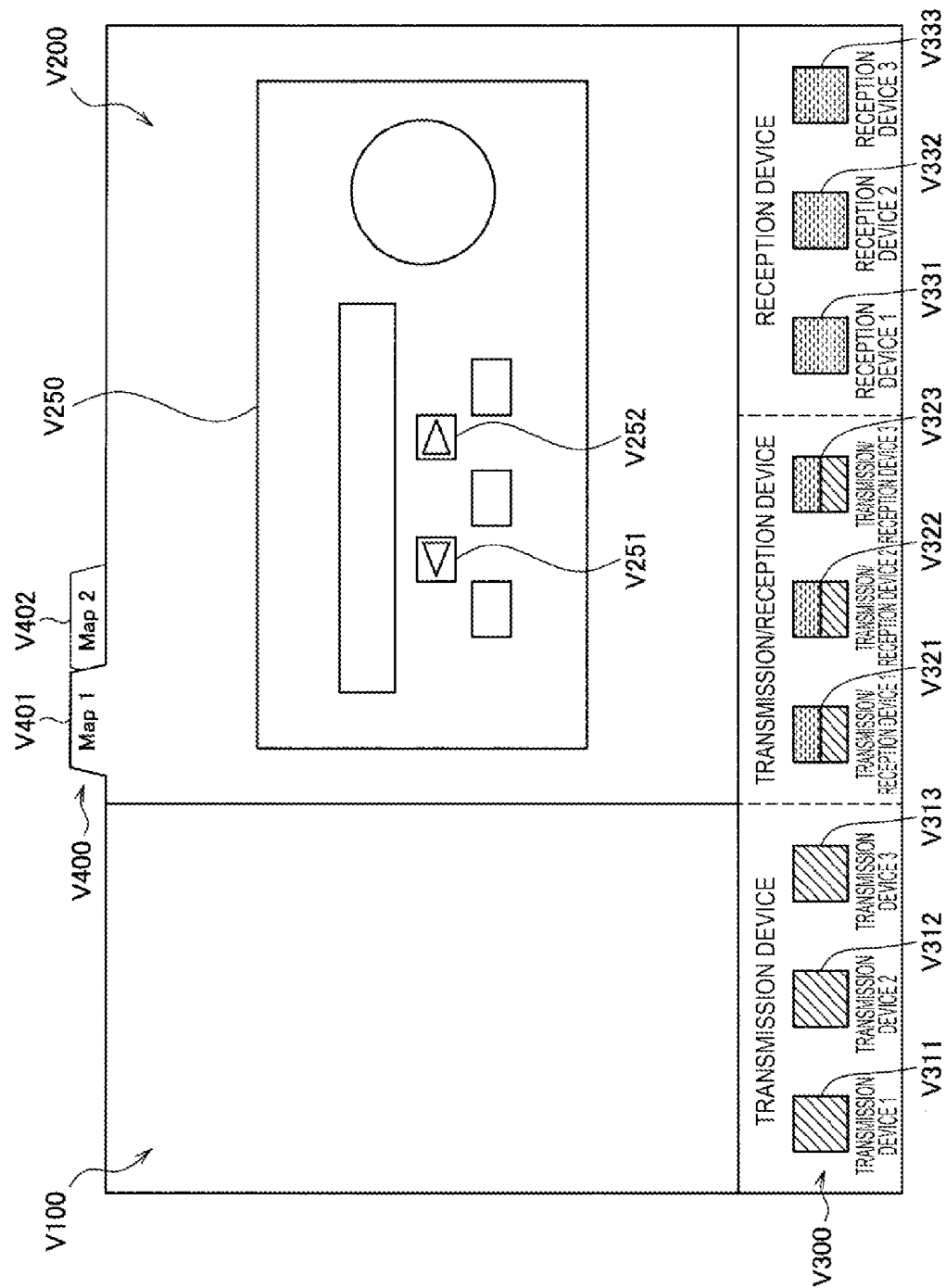
FIG. 13 is an explanatory diagram illustrating the second specific example according to the embodiment.

Note that, although the example in which the setting screen is displayed in the display area V100 has been described above, the setting screen may be displayed in the display area V200 as illustrated in FIG. 13. For example, the state may transition to a state illustrated in FIG. 13 in the case where predetermined user operation is performed on the icon V241 included in the layout screen in the state illustrated in FIG. 3. Note that, the predetermined user operation is different from user operation for causing the setting screen to be displayed in the display area V100. For example, in the case where the operation unit 30 is a mouse, the predetermined operation may be double click, right click, or the like. In the case where the operation unit 30 is a touchscreen, the predetermined operation may be long press on the touchscreen.

In a way similar to the icon V110 illustrated in FIG. 11, the icon V250 illustrated in FIG. 13 has appearance similar to the actual operation unit of the surgery device 2 corresponding to the icon V241. In addition, for example, in the case where the user performs selection operation on a button V251, a button V252, or the like, the device control unit 16 may generate a control signal for carrying out control regarding a setting of the surgery device 2 corresponding to the icon V241 in accordance with the selection operation. Such a configuration enables the user to perform operation regarding the settings of the surgery device 2 by using a larger setting screen.

4-3. Third Specific Example

Next, an example in which user operation for controlling inter-device connection is performed by using the preview screen will be described as a third specific example with reference to FIG. 14 to FIG. 23. FIG. 14 to FIG. 23 are explanatory diagrams illustrating the third specific example according to the present embodiment.

Figure 14:
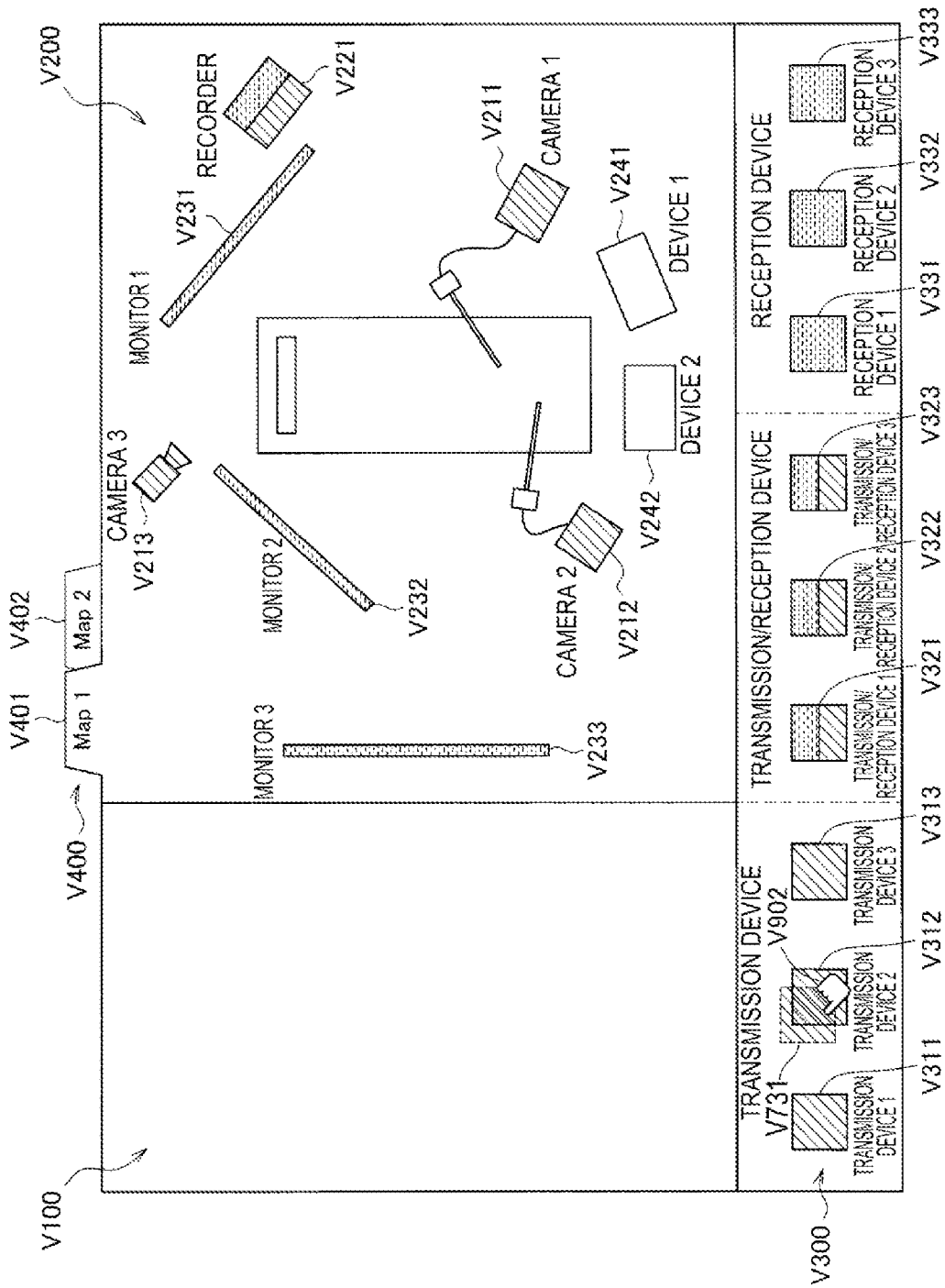
FIG. 14 is an explanatory diagram illustrating a third specific example according to the embodiment.

The example in FIG. 14 illustrates a state in which drag operation is performed on the icon V312 included in the device list screen by using the mouse cursor V902 in the state illustrated in FIG. 3, and a drag icon V731 corresponding to the icon V312 is displayed. Here, as described above, the surgery device 2 corresponding to the icon V312 has the function of transmitting images. In this specific example, sometimes the surgery device 2 corresponding to the icon V312 may be referred to as a first device. In addition, in this specific example, the first device is a recorder that stores images captured before surgery.

Figure 15:
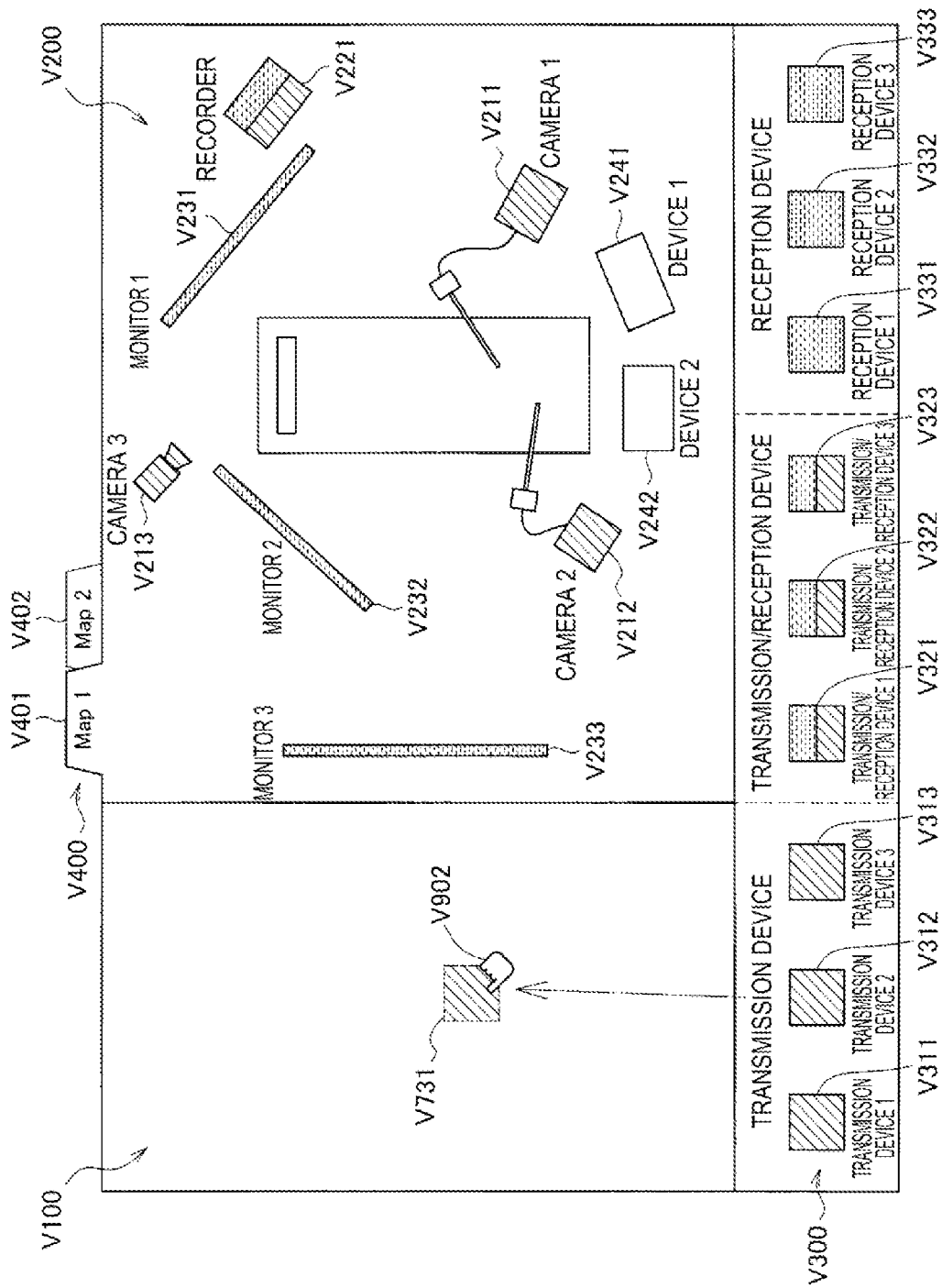
FIG. 15 is an explanatory diagram illustrating the third specific example according to the embodiment.

Next, FIG. 15 illustrates a state in which the mouse cursor V902 is moved in the state illustrated in FIG. 14 and drag operation is performed such that the drag icon V731 enters the display area V100. When the drop operation is performed in the state illustrated in FIG. 15, the state transitions to a state illustrated in FIG. 16. In the state illustrated in FIG. 16, the display control unit 14 causes a preview screen to be displayed in the display area V100. The preview screen includes images transmitted from the first device.

Figure 16:
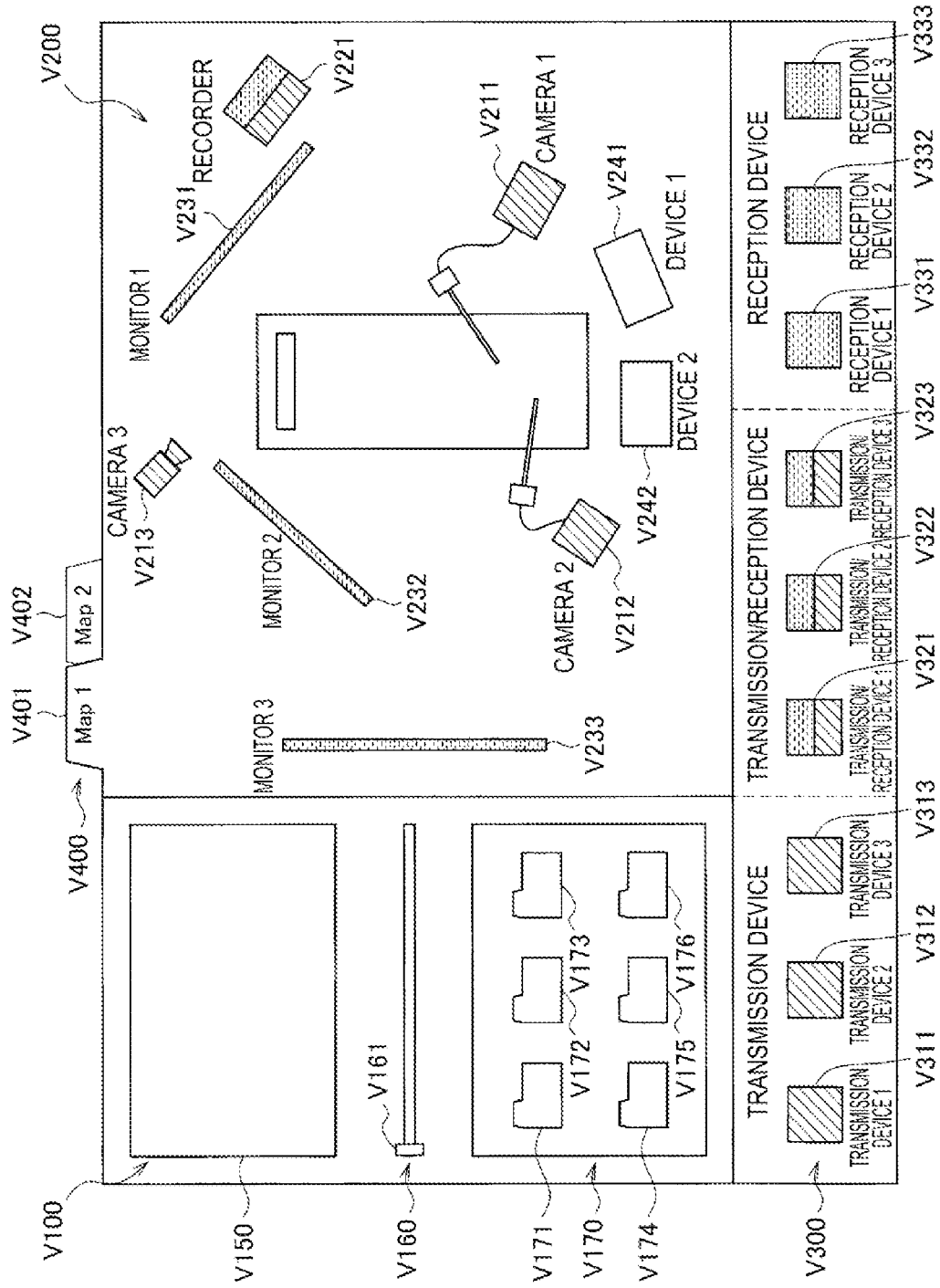
FIG. 16 is an explanatory diagram illustrating the third specific example according to the embodiment.

As illustrated in FIG. 16, the preview screen displayed in the display area V100 includes a preview display area V150, a playback position designation interface V160 for designating a playback position, and an image selection screen V170. In addition, as illustrated in FIG. 16, the playback position designation interface V160 includes a slider V161. The image selection screen V170 includes icons V171 to V176 corresponding to images stored in the first device.

Figure 17:
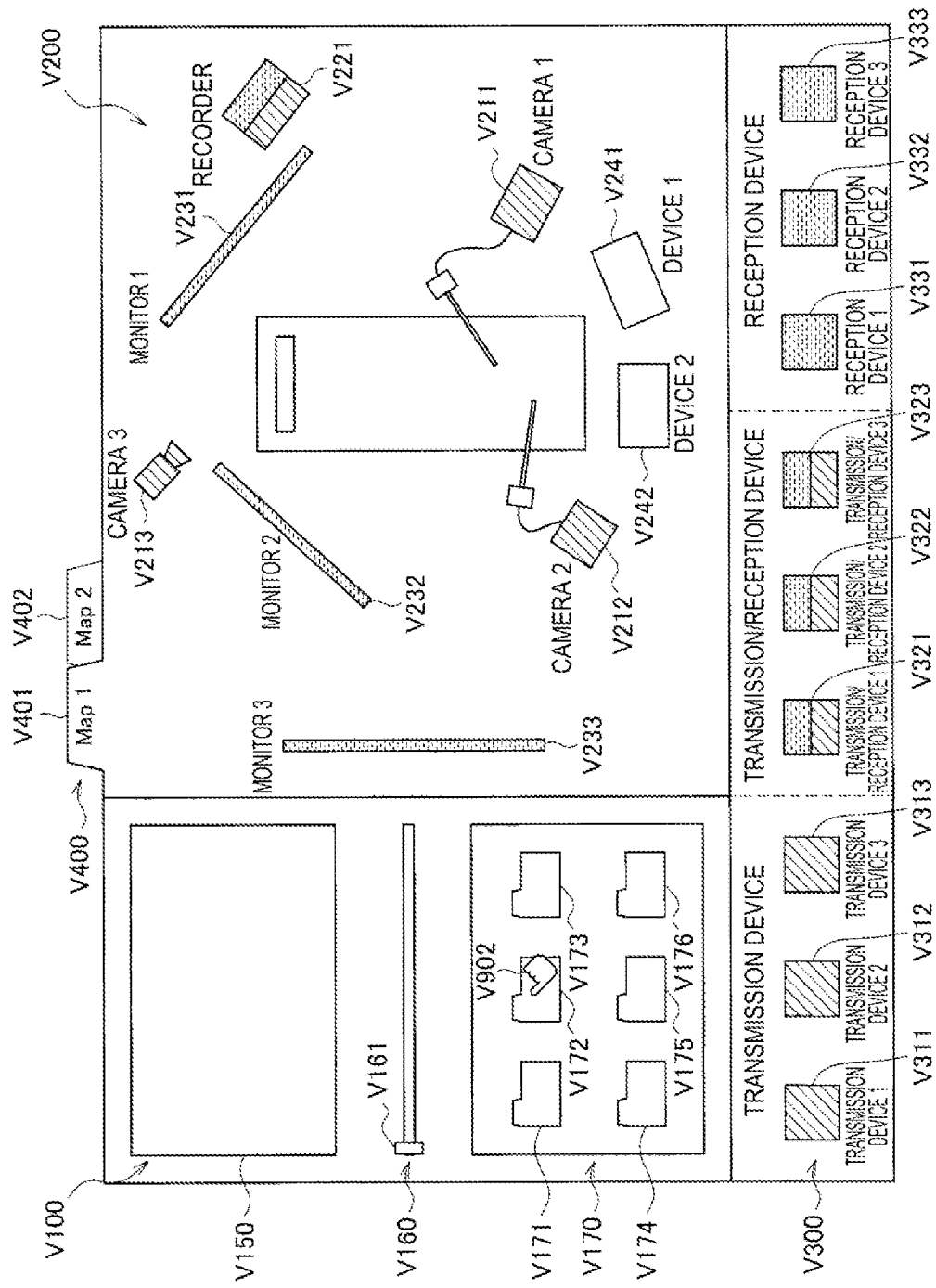
FIG. 17 is an explanatory diagram illustrating the third specific example according to the embodiment.
Figure 18:
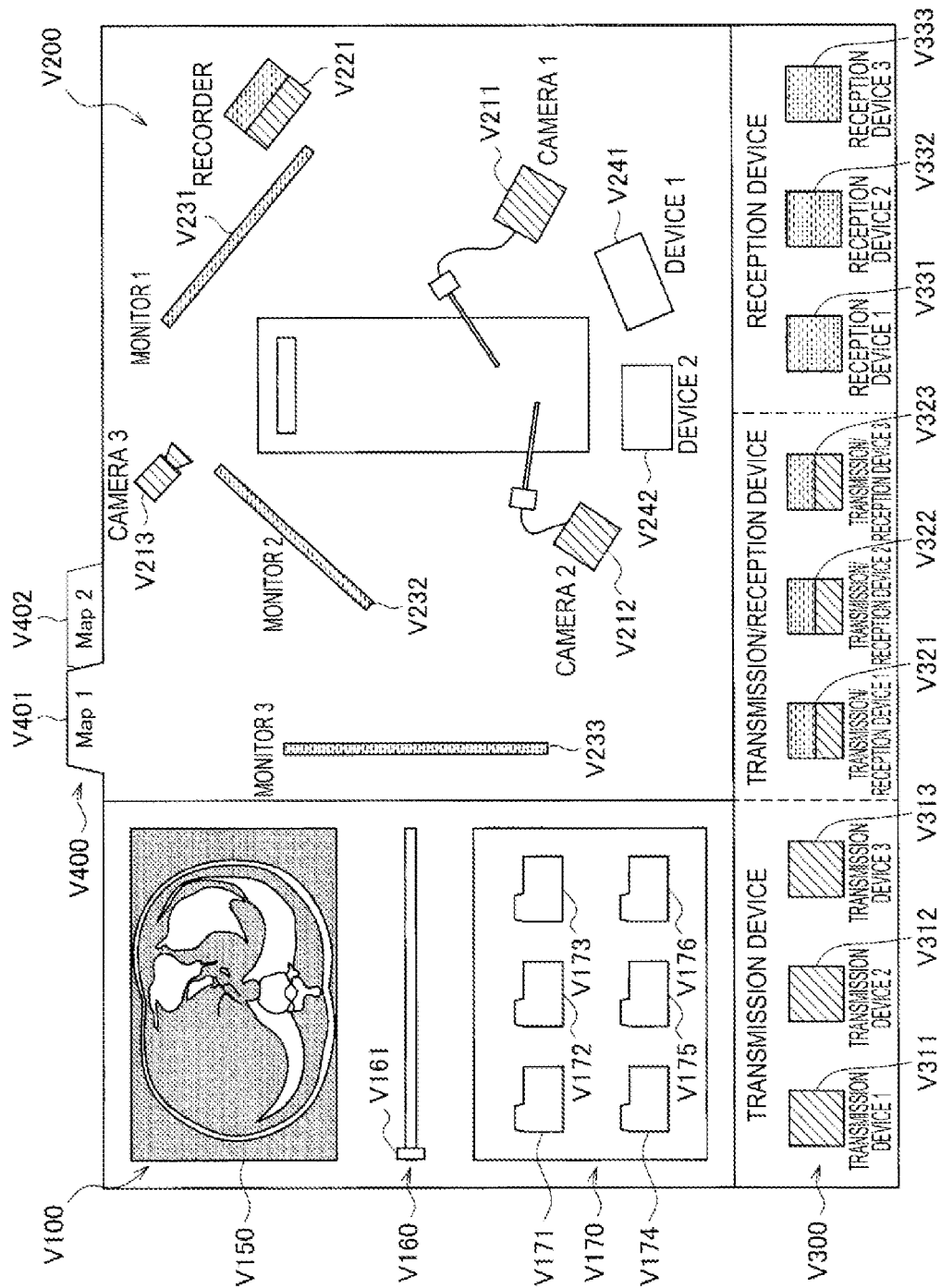
FIG. 18 is an explanatory diagram illustrating the third specific example according to the embodiment.

As illustrated in FIG. 17, when selection operation is performed on the icon V172 by using the mouse cursor V902, the display control unit 14 causes an image corresponding to the icon V172 to be displayed in the preview display area V150, and the state transitions to a state illustrated in FIG. 18.

Figure 19:
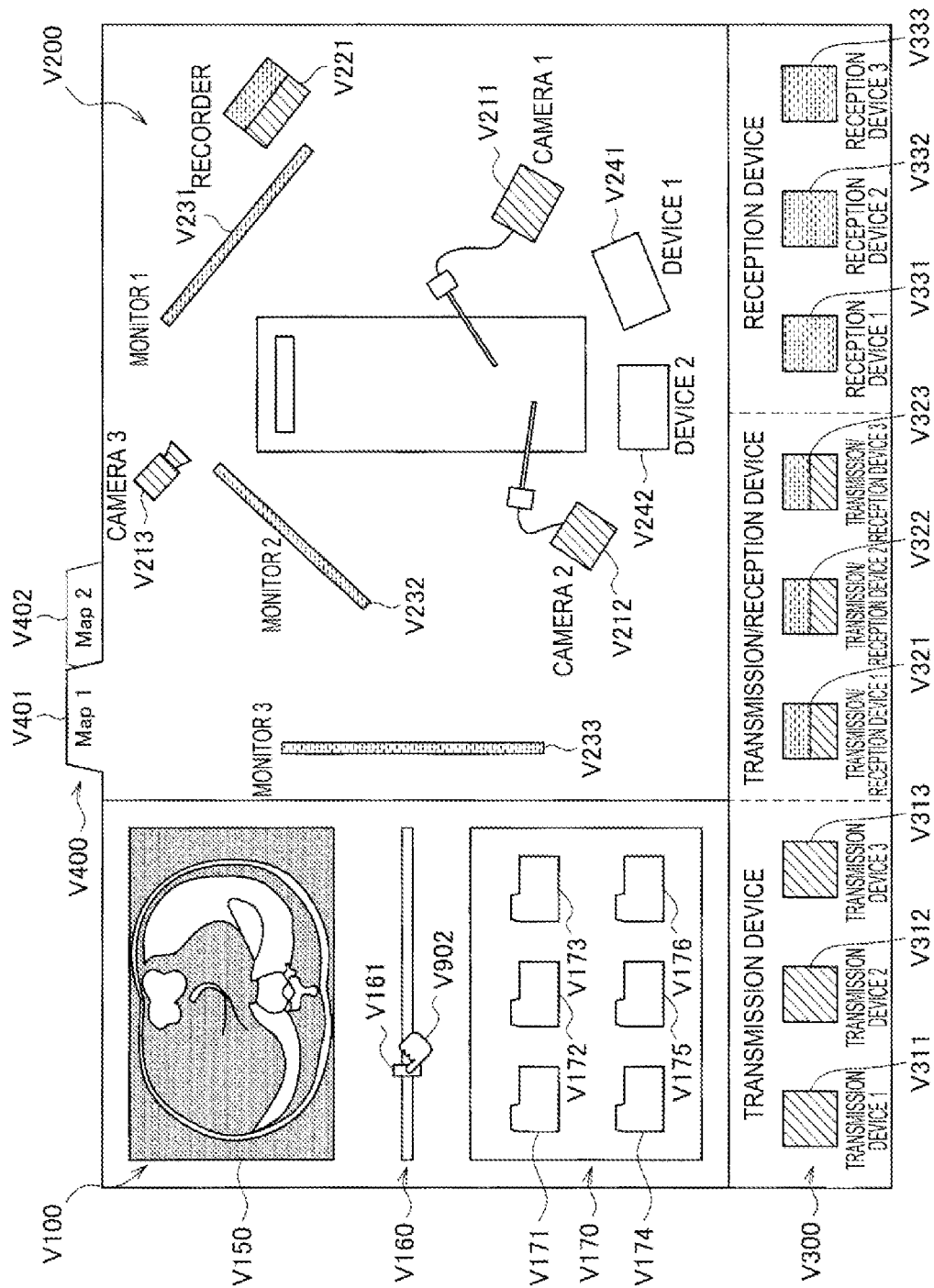
FIG. 19 is an explanatory diagram illustrating the third specific example according to the embodiment.

FIG. 19 illustrates a state in which drag operation is performed on the slider V161 of the reproduction position designation interface V160 by using the mouse cursor V902 in the state illustrated in FIG. 18. In the case where the image is a moving image, the display control unit 14 causes a frame corresponding to the position of the slider V161 to be displayed in the preview display area V160 among images corresponding to the icon V172 as illustrated in FIG. 19. Such a configuration enables the user to see the image transmitted from the first device in the preview screen, and enables the user to designate a frame in the case where the image is a moving image.

Figure 20:
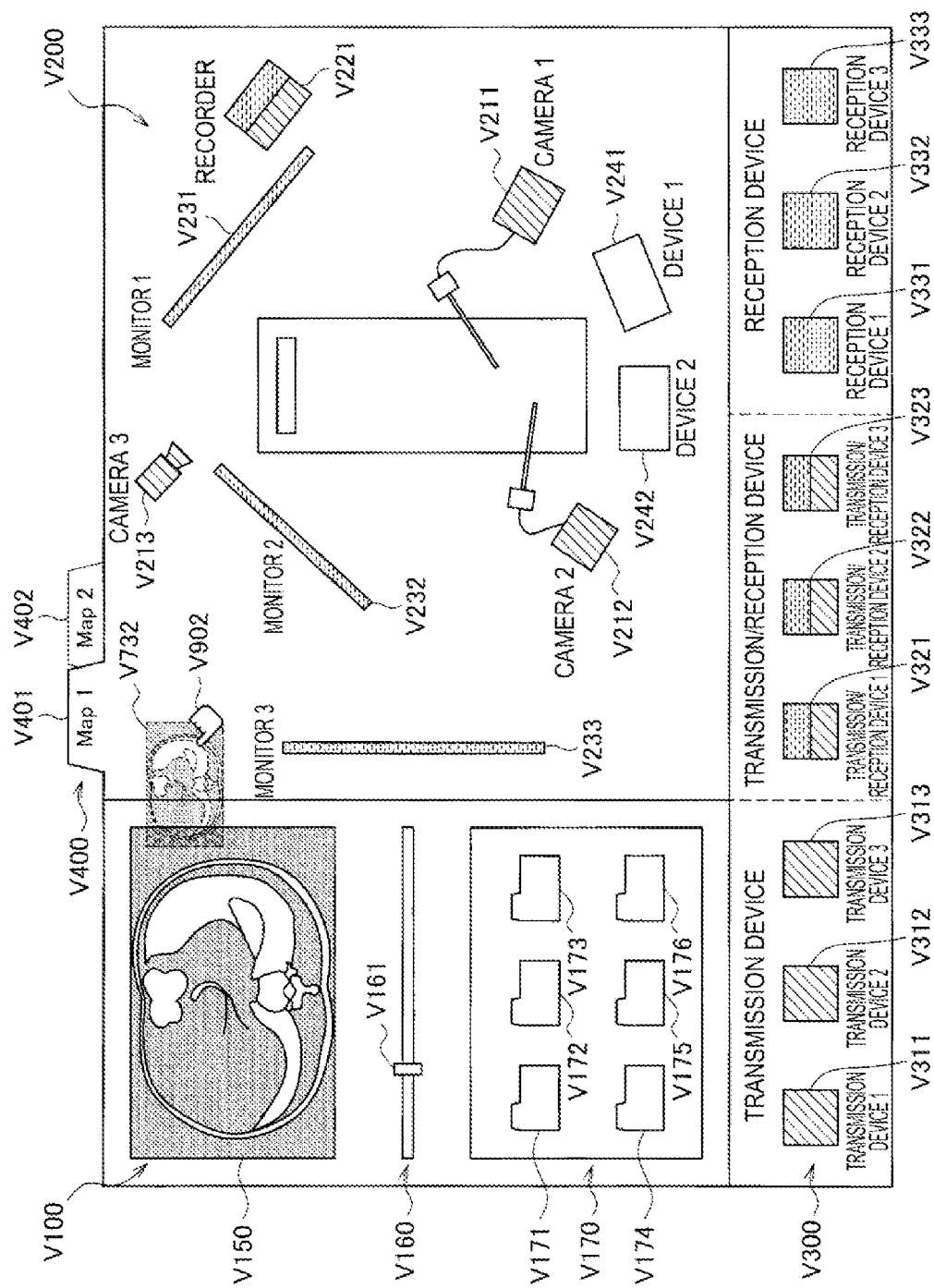
FIG. 20 is an explanatory diagram illustrating the third specific example according to the embodiment.

FIG. 20 illustrates a state in which drag operation is performed on the preview display area V150 by using the mouse cursor V902 in the state illustrated in FIG. 19, and a drag icon V732 corresponding to the image displayed in the preview display area V150 is displayed.

Figure 21:
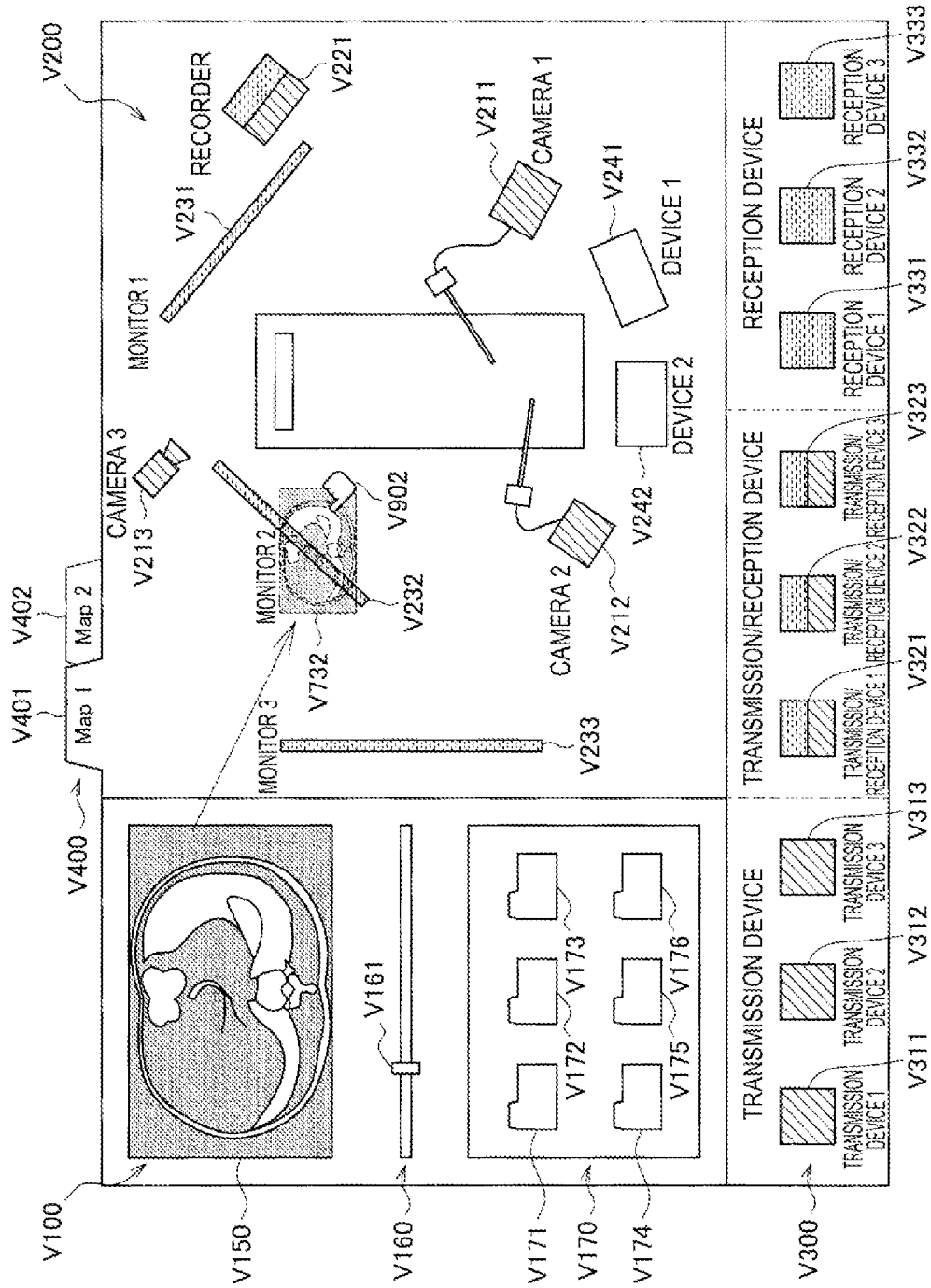
FIG. 21 is an explanatory diagram illustrating the third specific example according to the embodiment.

Next, FIG. 21 illustrates a state in which the mouse cursor V902 is moved in the state illustrated in FIG. 19 and drag operation is performed such that the drag icon V732 overlaps the icon V232. Here, as described above, the surgery device 2 corresponding to the icon V232 is a monitor having the function of receiving images. In this specific example, the surgery device 2 corresponding to the icon V232 may be referred to as a second device. In addition, in a way similar to the above-described first specific example, the second device is capable of dividing the display area into four areas and simultaneously displaying a maximum of four images also in this specific example.

Figure 22:
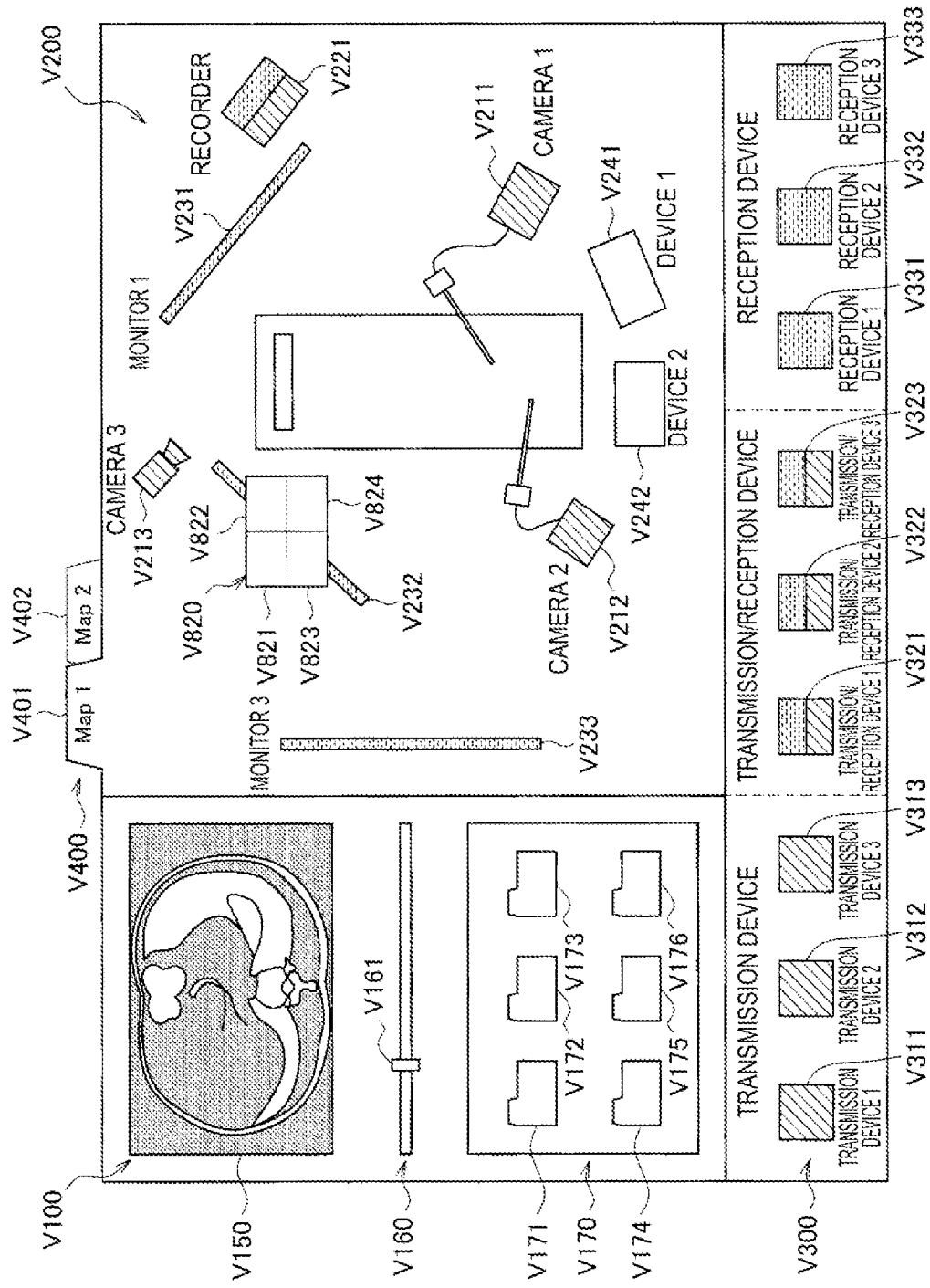
FIG. 22 is an explanatory diagram illustrating the third specific example according to the embodiment.

When the drop operation is performed in the state illustrated in FIG. 21, the state transitions to a state illustrated in FIG. 22. In the state of FIG. 22, the display control unit 14 causes a display area selection screen V820 to be displayed. The display area selection screen V820 is a pop-up screen for selecting a display position of an image transmitted from the first device to the second device in the second device. In a way similar to the display area selection screen V810 described with reference to FIG. 7, the display area selection screen V820 includes display positions in the second device, in other words, divided areas V821 to V824 corresponding to divided display areas.

Figure 23:
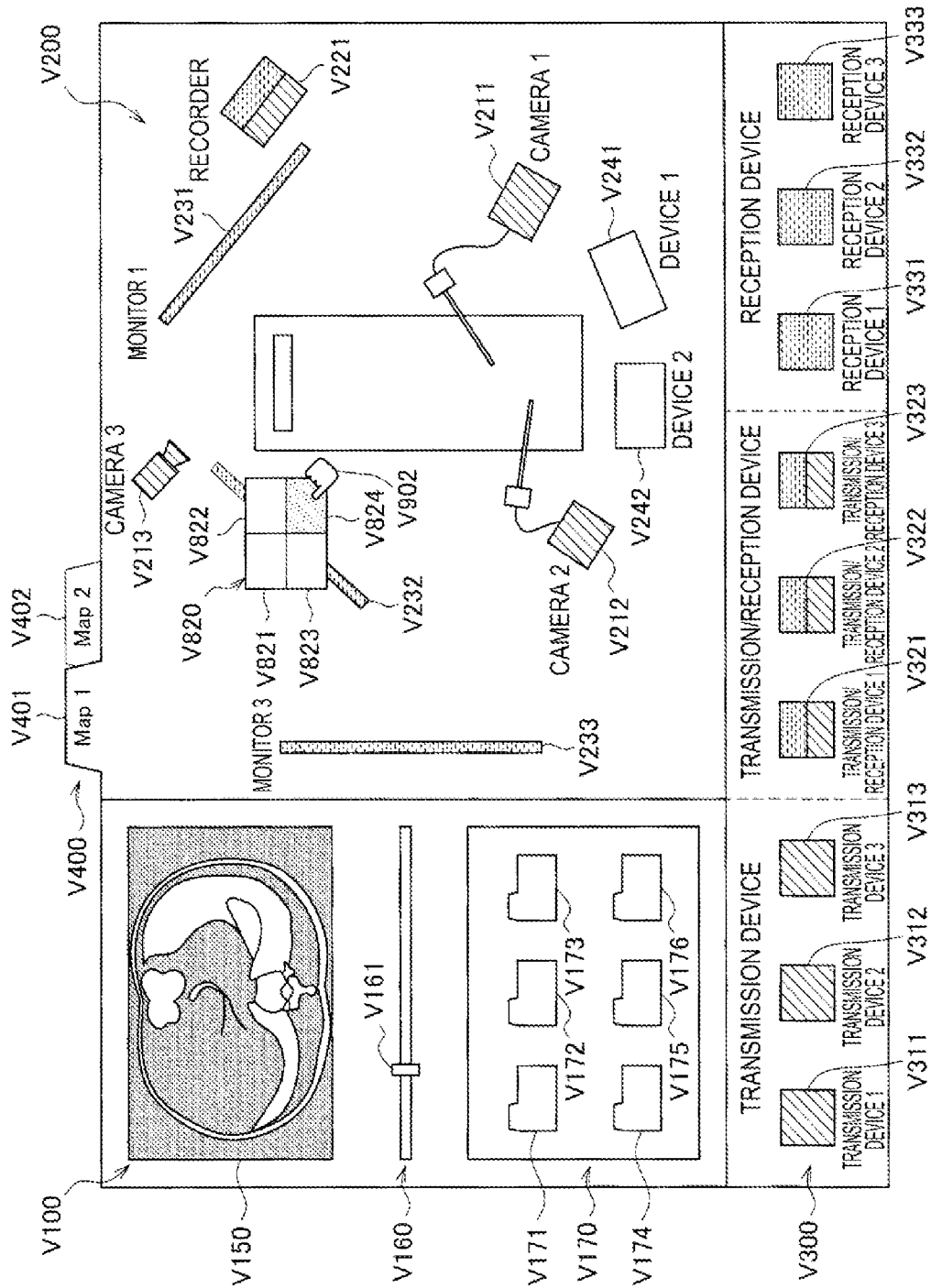
FIG. 23 is an explanatory diagram illustrating the third specific example according to the embodiment.

FIG. 23 illustrates a state in which selection operation is performed on the divided area V824 included in the display area selection screen V820 in the state illustrated in FIG. 22. The device control unit 16 may generate a control signal for controlling inter-device connection such that the first device transmits an image to the second device, on the basis of the above-described series of user operation performed on the icon V312 corresponding to the first device, the preview display area V150 included in the preview screen, and the icon V232 corresponding to the second device. Such a configuration enables performing intuitive operation for inter-device connection, seeing images displayed in advance on the second device, and designating a frame.

In addition, in the case where the above-described selection operation is performed on the display area selection screen V820 in a way similar to the above-described first specific example, the device control unit 16 may generate a control signal for carrying out control regarding a display position in the second device on the basis of the selection operation.

In addition, in the case where the second device is a monitor for displaying an image on the entire display area in a way similar to the above-described first specific example, the device control unit 16 may generate a control signal for controlling the inter-device connection such that the first device transmits an image to the second device at a time when the drop operation is performed in the state illustrated in FIG. 21.

4-4. Fourth Specific Example

Next, an example of performing user operation regarding switch of display of a plurality of layout screens will be described as a fourth specific example with reference to FIG. 24 to FIG. 27. FIG. 24 to FIG. 27 are explanatory diagrams illustrating the fourth specific example according to the present embodiment.

Figure 24:
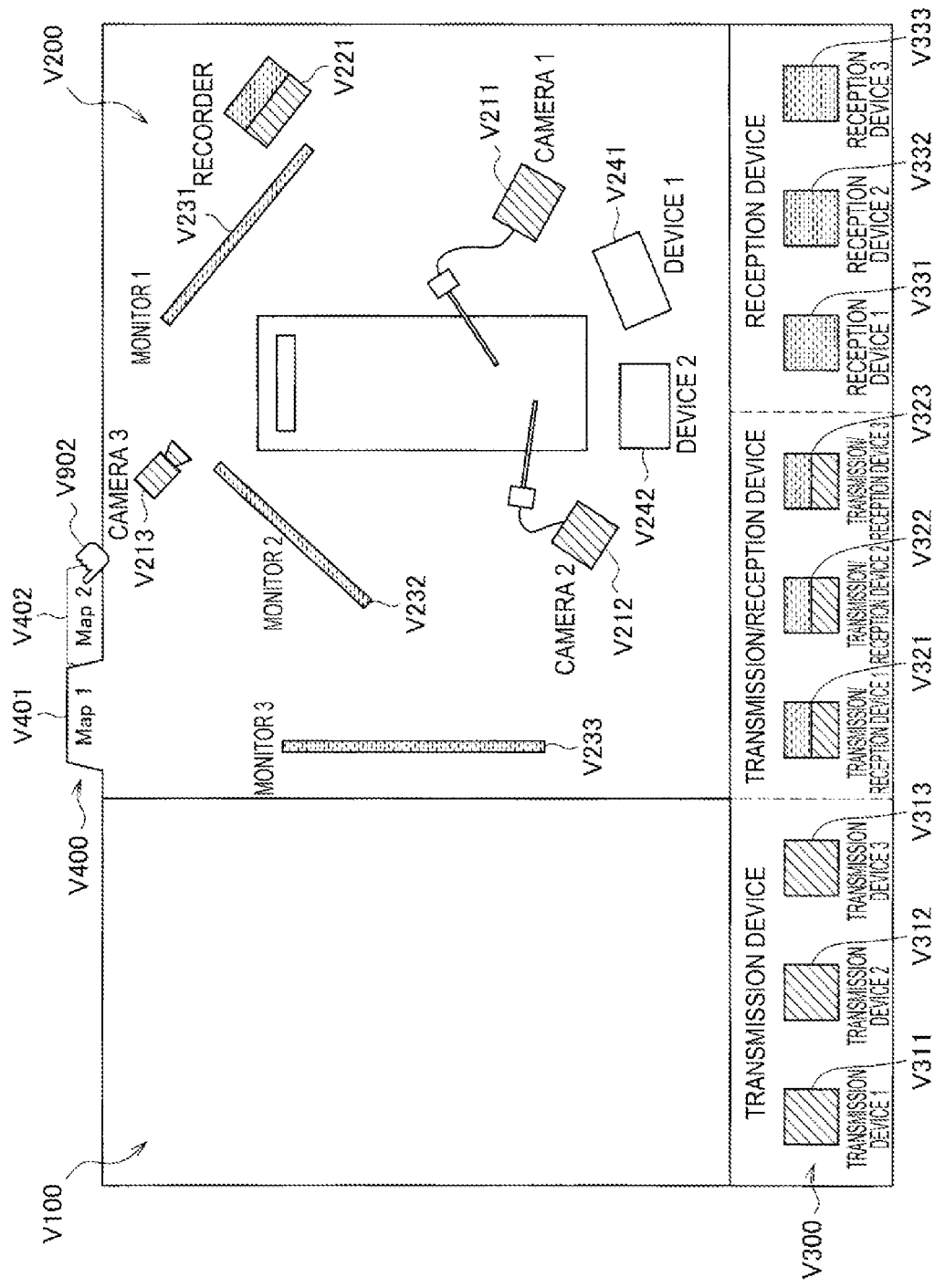
FIG. 24 is an explanatory diagram illustrating a fourth specific example according to the embodiment.

FIG. 24 illustrates a state in which the mouse cursor V902 is moved to the position of the tab V402 in the state illustrated in FIG. 3. When the user performs selection operation on the tab V402 in the state illustrated in FIG. 24, the display control unit 14 switches the display of the layout screen displayed in the display area V200, and the state transitions to a state illustrated in FIG. 25.

Figure 25:
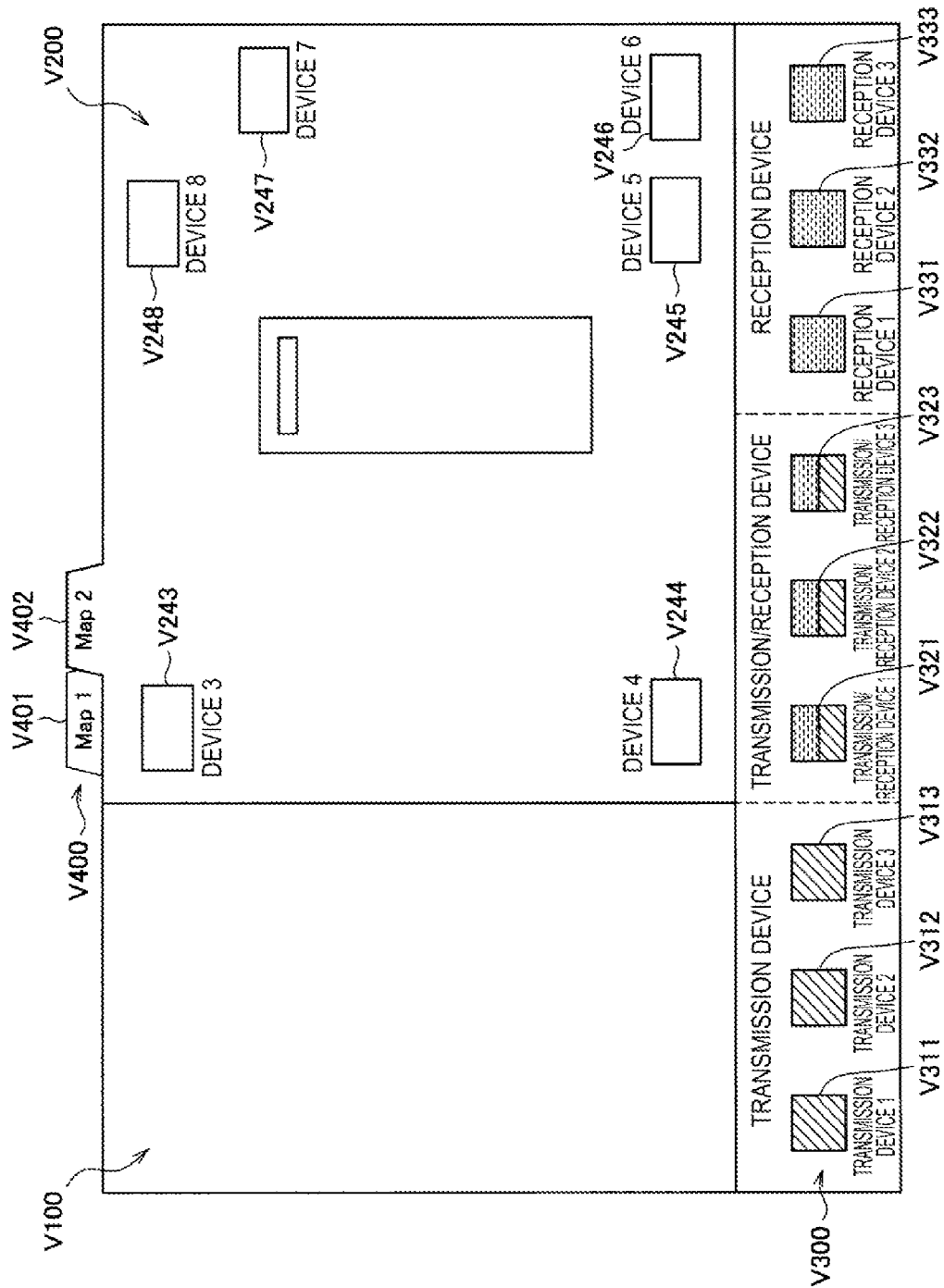
FIG. 25 is an explanatory diagram illustrating the fourth specific example according to the embodiment.

In the state illustrated in FIG. 25, the layout screen displayed in the display area V200 shows arrangement of surgery devices 2 that are present in the surgery room but not shown in the layout screen displayed in the display area V200 in the state illustrated in FIG. 24, for example. Specifically, FIG. 25 illustrates icons V243 to V247 corresponding to the surgery devices 2 that are not illustrated in FIG. 24.

The layout screen displayed in FIG. 25 may be a layout screen captured from a viewpoint different from the layout screen illustrated in FIG. 24. For example, the surgery devices 2 corresponding to the icons V243 to V247 displayed in FIG. 25 may be surgery devices 2 installed at heights different from the surgery devices 2 corresponding to the icons included in the layout screen displayed in the display area V200 in the state illustrated in FIG. 24.

However, the present technology is not limited thereto. The surgery devices 2 corresponding to the icons V243 to V247 may be different types of surgery devices 2 from the surgery devices 2 corresponding to the icons included in the layout screen displayed in the display area V200 in the state illustrated in FIG. 24. In addition, although FIG. 25 illustrates the example of displaying the layout screen showing arrangement of surgery devices 2 present in the surgery room, the present technology is not limited thereto. For example, by switching the display of the layout screen in accordance with the tab selection operation, a layout screen showing arrangement of surgery devices 2 present outside of the surgery room may be displayed.

Figure 26:
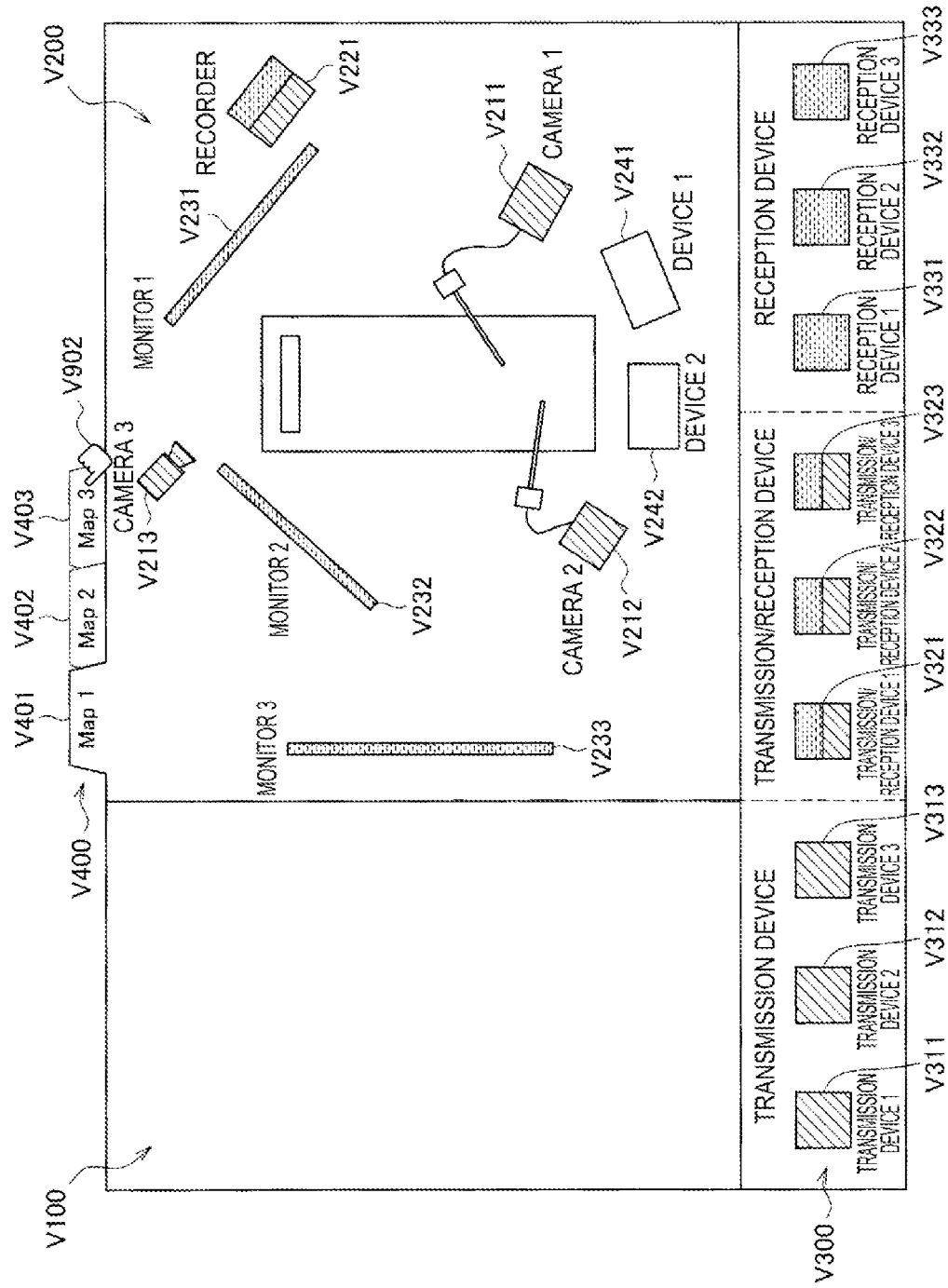
FIG. 26 is an explanatory diagram illustrating the fourth specific example according to the embodiment.

In addition, although the example in which only the two tabs V401 and V402 are displayed in the display area V400 has been described above, a larger number of tabs may be displayed. For example, as illustrated in FIG. 26, three tabs including tabs V401 to V403 may be displayed in the display area V400. In addition, when the user performs selection operation on the tab V403 in the state illustrated in FIG. 26, the display control unit 14 may switch the display of the layout screen displayed in the display area V200, and the state may transition to a state illustrated in FIG. 27.

Figure 27:
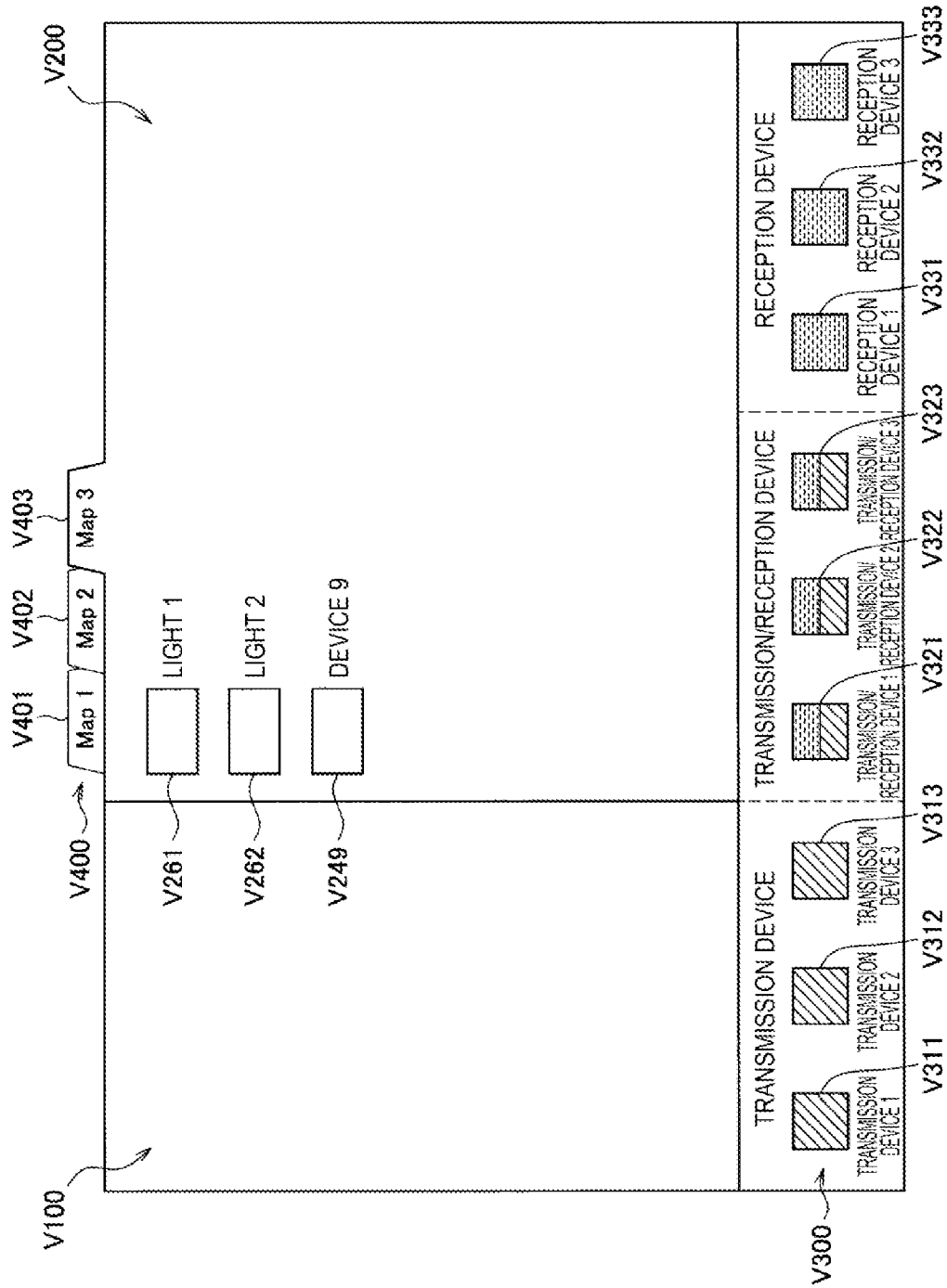
FIG. 27 is an explanatory diagram illustrating the fourth specific example according to the embodiment.

In the example illustrated in FIG. 27, a device list screen is displayed in the display area V200. The device list screen includes icons V249, V261, and V262 corresponding to surgery devices 2. The surgery devices 2 corresponding to the icons V249, V261, and V262 are present in a surgery room, but it is difficult to display arrangement of the surgery devices 2 corresponding to the icons V249, V261, and V262. Note that, for example, such surgery devices 2 that are present in the surgery room but whose arrangement is difficult to be displayed may be surgery devices 2 present in a wide range, surgery devices 2 that are moved frequently during surgery, or the like. Such a configuration enables performing operation for carrying out control also regarding surgery devices 2 that are present in the surgery room but whose arrangement is difficult to be displayed.

As described above, the respective layout screens may show arrangement of different surgery devices 2 among a plurality of surgery devices 2 included in the surgery system 1000. The surgery devices 2 shown in the respective layout screens may be classified on the basis of a predetermined standard.

4-5. Fifth Specific Example

Figure 28:
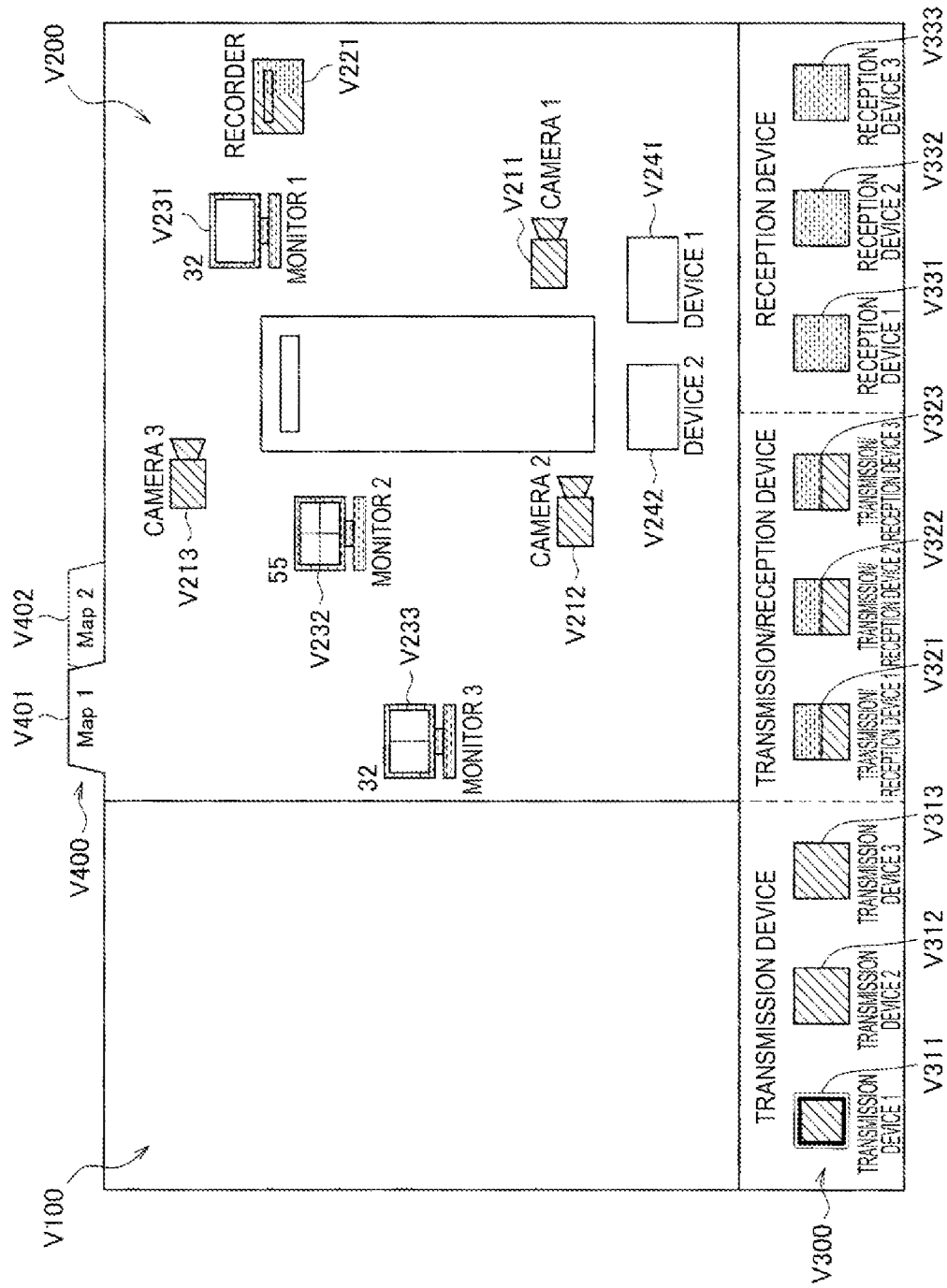
FIG. 28 is an explanatory diagram illustrating a fifth specific example according to the embodiment.

Next, an example in which the display control unit 14 causes an icon different from the above-described icons to be displayed will be described as a fifth specific example with reference to FIG. 28. FIG. 28 is an explanatory diagram illustrating the fifth specific example according to the present embodiment.

The example illustrated in FIG. 28 is an example in which the layout screen displayed on the display area V200 includes icons that are simpler than the above-described examples. Note that, in the example illustrated in FIG. 28, icons corresponding to the same surgery devices 2 as the above-described surgery devices 2 are denoted with the same reference signs as the above-described icons in FIG. 3 or the like.

In addition, in the example illustrated in FIG. 28, the layout screen displayed on the display area V200 shows positions of the surgery devices 2, but does not show attitudes of the surgery devices 2. For example, the icons included in the layout screen displayed in the display area V200 may be displayed not with attitudes corresponding to actual attitudes of the surgery devices 2 but with predetermined attitudes, for example. For example, the layout screen illustrated in FIG. 28 is useful in the case where positions of the surgery devices 2 are not changed during surgery but attitudes of the surgery devices 2 are often changed during surgery. In addition, in the example illustrated in FIG. 28, although the attitudes are not shown, it is easier to recognize types of the surgery devices 2 corresponding to the respective icons.

In addition, in the example illustrated in FIG. 28, the icons V231 to V233 corresponding to monitors (examples of the surgery devices 2) have functions of showing how the display areas of the monitors corresponding to the respective icons are divided (how many images can be simultaneously displayed at maximum). In addition, in the example illustrated in FIG. 28, numerical values representing sizes of the monitors corresponding to the respective icons are displayed near the icons V231 to V233. Such a configuration enables the user to easily recognize information regarding the surgery devices 2.

In addition, in this specific example, the display control unit 14 may cause an icon corresponding to a surgery device 2 to be displayed on the basis of whether or not the surgery device 2 is in a state capable of transmitting currently capturing images.

For example, in the example illustrated in FIG. 28, icons included in the device list screen displayed in the display area V300 are displayed such that states of the icons are distinguishable on the basis of shapes of the icons. Specifically, the icon V311 indicates that the surgery device 2 corresponding to the icon is in the state capable of transmitting currently capturing images.

Such a configuration enables the user to easily recognize whether or not a surgery device 2 corresponding to an icon is in the state capable of transmitting currently capturing images.

Note that, in a similar way, the display control unit 14 may cause an icon corresponding to a surgery device 2 to be displayed on the basis of whether or not the surgery device 2 is in a state capable of transmitting images that are stored in advance.

4-6. Sixth Specific Example

Next, an example in which the display control unit 14 causes a layout screen showing arrangement of surgery devices 2 present in a surgery room and a layout screen showing arrangement of surgery devices 2 present outside of the surgery room to be simultaneously displayed, will be described as a sixth specific example with reference to FIG. 29 to FIG. 35. FIG. 29 to FIG. 35 are explanatory diagrams illustrating the sixth specific example according to the present embodiment.

Figure 29:
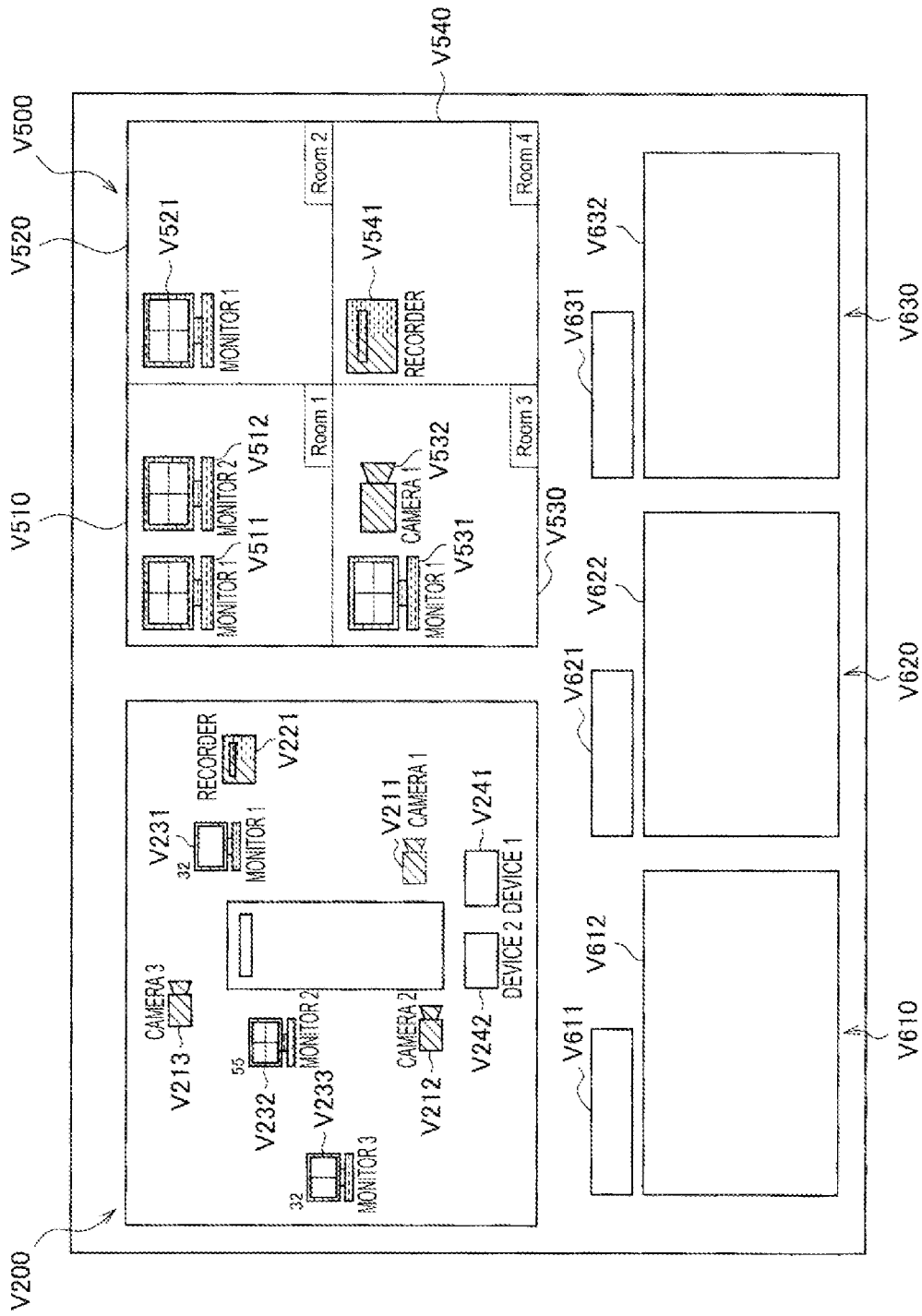
FIG. 29 is an explanatory diagram illustrating a sixth specific example according to the embodiment.

In the example illustrated in FIG. 29, the layout screen showing arrangement of surgery devices 2 present in the surgery room is displayed in the display area V200, and the layout screen showing arrangement of surgery devices 2 present outside of the surgery room is displayed in a display area V500. The display area V500 includes four display areas V510, V520, V530, and V540. A layout screen including icons corresponding to surgery devices 2 present in a different room is displayed in each of the four display areas.

For example, the layout screen displayed in the display area V510 includes icons V511 and V512 corresponding to monitors. In addition, the layout screen displayed in the display area V520 includes an icon V521 corresponding to a monitor. In addition, the layout screen displayed in the display area V530 includes an icon V531 corresponding to a monitor and an icon V532 corresponding to a camera. In addition, the layout screen displayed in the display area V540 includes an icon V541 corresponding to a recorder.

Note that, in FIG. 29, simplified icons are used in a way similar to the example illustrated in FIG. 28. In addition, in the example illustrated in FIG. 29, icons corresponding to the same surgery devices 2 as the above-described surgery devices 2 are denoted with the same reference signs as the above-described icons in FIG. 28.

In addition, in the example illustrated in FIG. 29, the display control unit 14 causes three preview screens V610, V620, and V630 to be displayed. The preview screens V610, V620, and V630 respectively include device name display areas V611, V621, and V631 and preview display areas V612, V622, and V632.

According to the specific example, it is possible to display a layout screen showing in which room the surgery devices 2 are present, the surgery devices 2 being present outside of the surgery room. Accordingly, it is easier for the user to recognize correspondence between the surgery devices 2 and icons.

In addition, also in this specification, it is also possible to perform user operation, control display in accordance with the user operation, and generate a control signal on the basis of the user operation, in a way similar to the above-described first to fourth specific examples.

Figure 30:
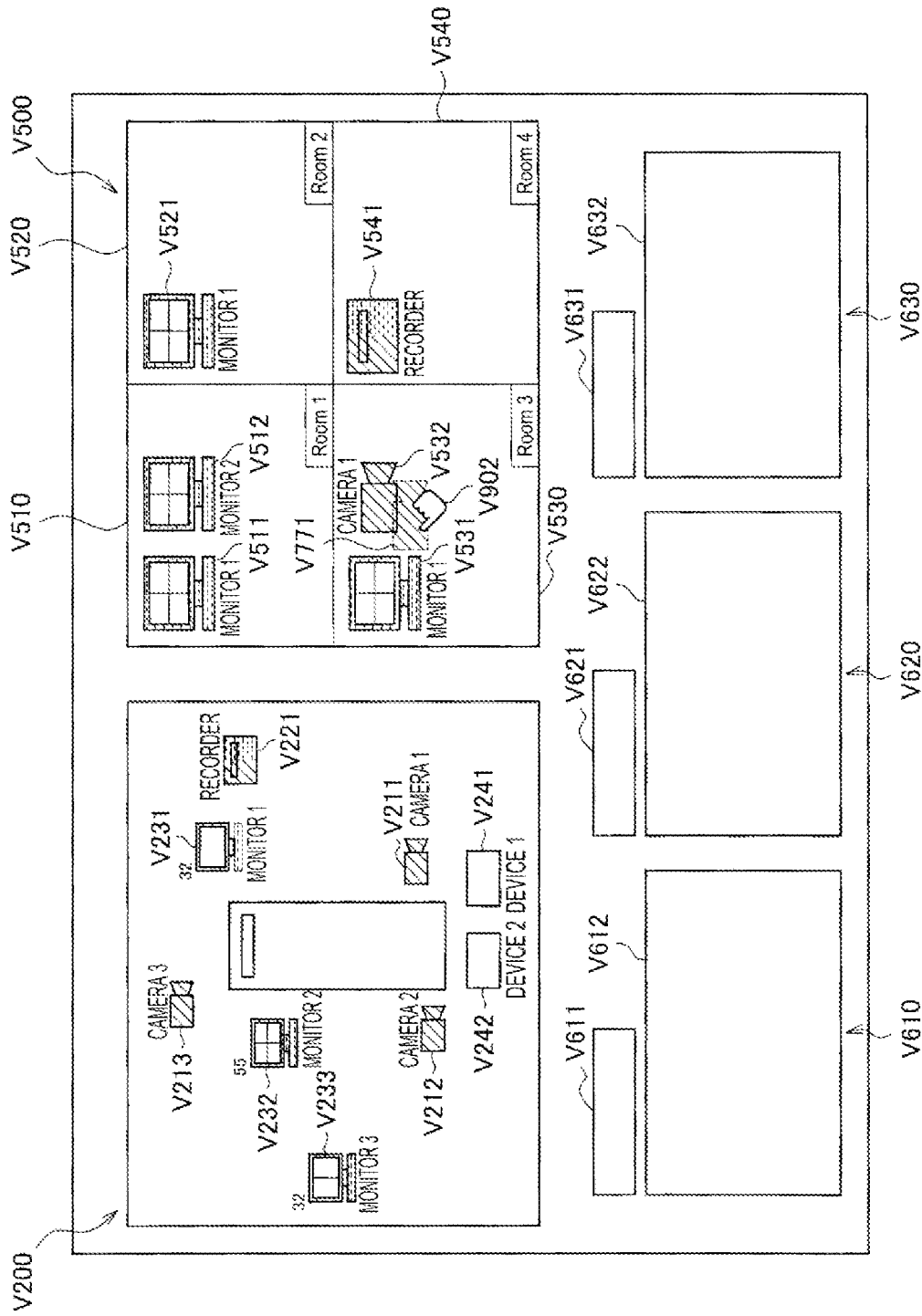
FIG. 30 is an explanatory diagram illustrating the sixth specific example according to the embodiment.

FIG. 30 illustrates a state in which drag operation is performed on the icon V532 included in a layout screen displayed in the display area V530 by using the mouse cursor V902 in the state illustrated in FIG. 29, and a drag icon V771 corresponding to the icon V532 is displayed. Here, as described above, the surgery device 2 corresponding to the icon V532 is a camera having the function of transmitting images. In this specific example, the surgery device 2 corresponding to the icon V532 may be referred to as a first device.

Figure 31:
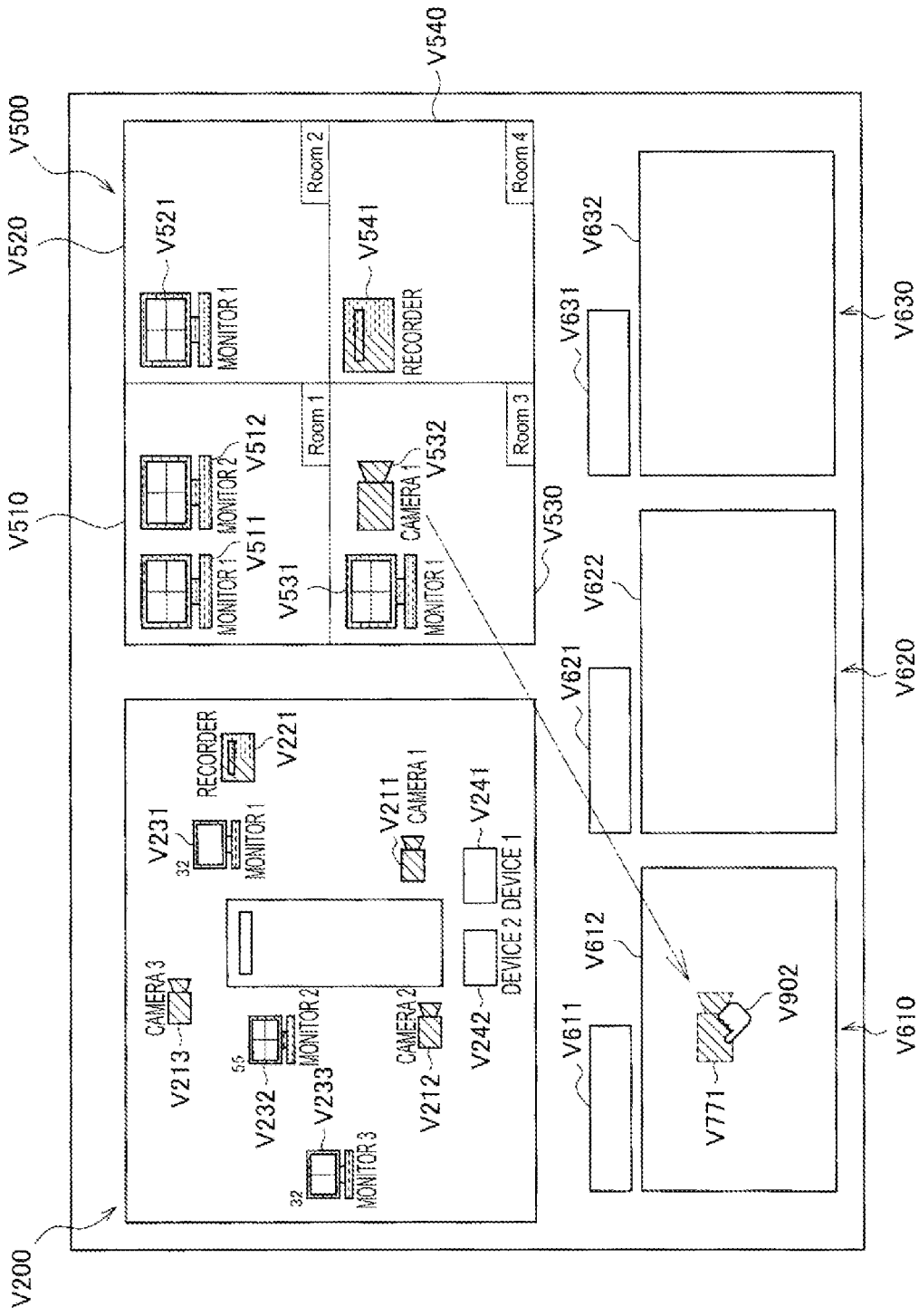
FIG. 31 is an explanatory diagram illustrating the sixth specific example according to the embodiment.

Next, FIG. 31 illustrates a state in which the mouse cursor V902 is moved in the state illustrated in FIG. 30 and drag operation is performed such that the drag icon V771 enters the preview screen V610. When the drop operation is performed in the state illustrated in FIG. 30, the state transitions to a state illustrated in FIG. 32. In the state illustrated in FIG. 32, the display control unit 14 causes an image transmitted from the first device to be displayed in the preview display area V612 in the preview screen V610. In addition, as illustrated in FIG. 32, the display control unit 14 may cause the device name of the first device to be displayed in the device name display area V611 in the preview screen V610.

Figure 32:
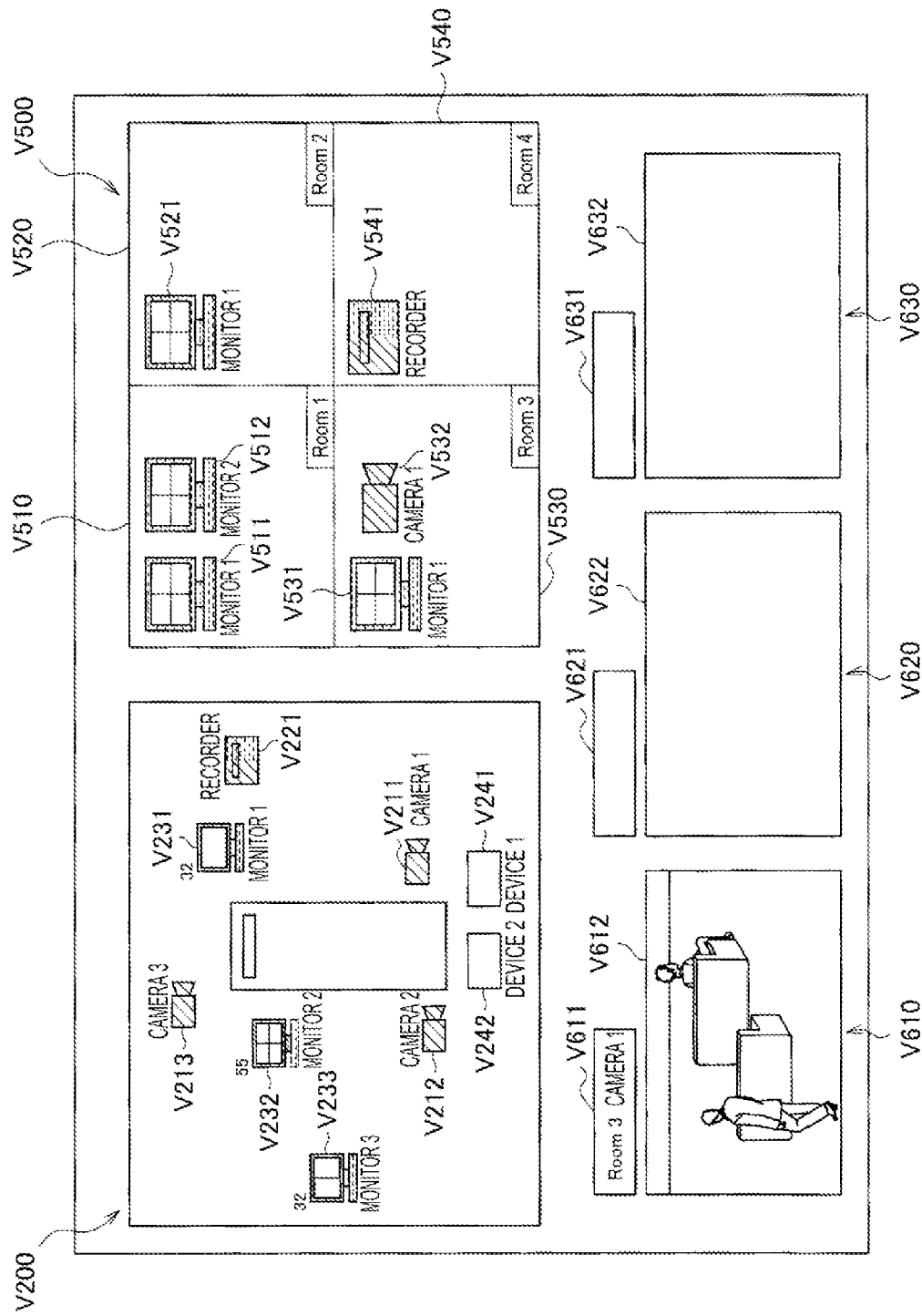
FIG. 32 is an explanatory diagram illustrating the sixth specific example according to the embodiment.
Figure 33:
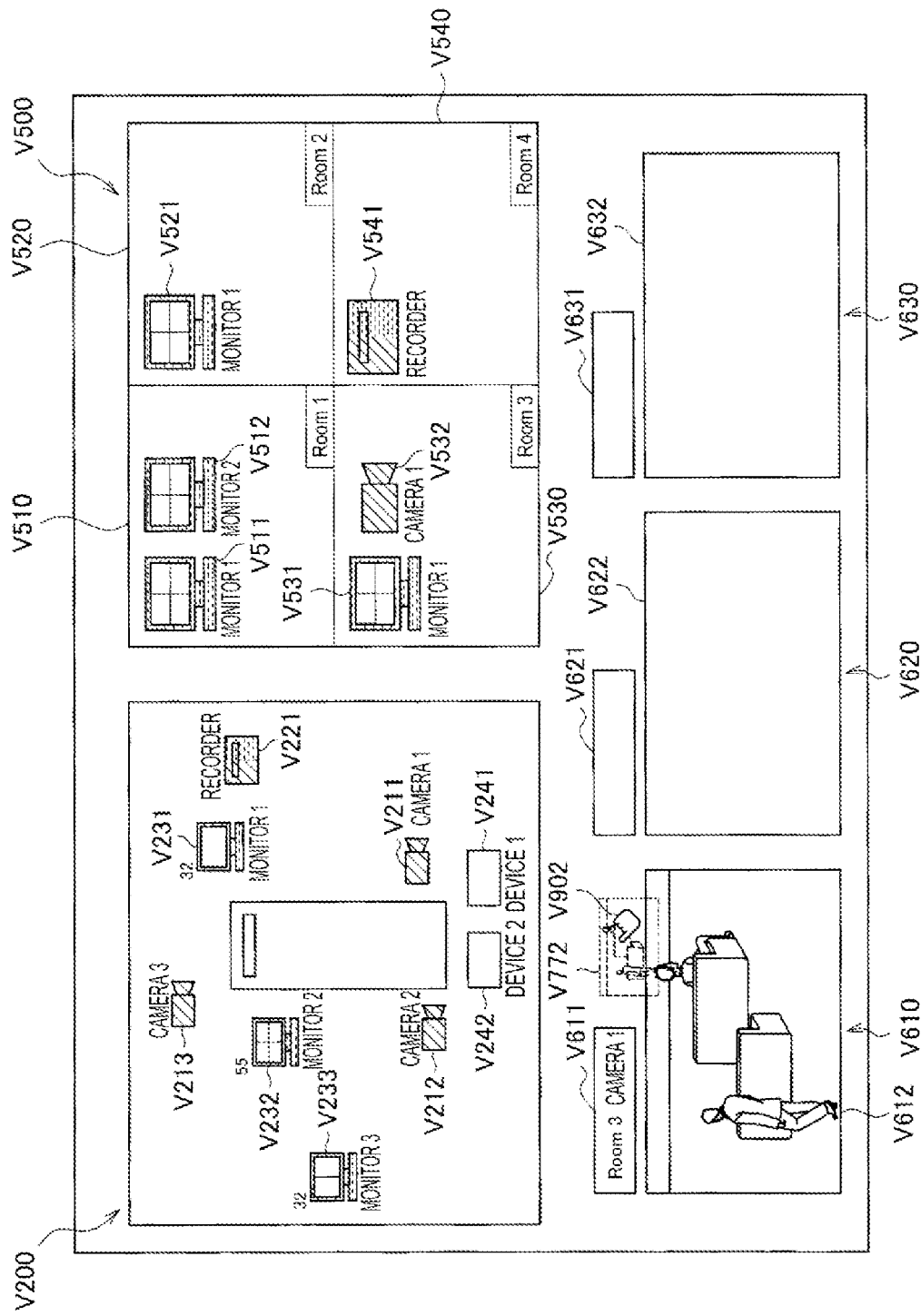
FIG. 33 is an explanatory diagram illustrating the sixth specific example according to the embodiment.

FIG. 33 illustrates a state in which drag operation is performed on the preview display area V612 by using the mouse cursor V902 in the state illustrated in FIG. 32, and a drag icon V772 corresponding to the image displayed in the preview display area V612 is displayed.

Figure 34:
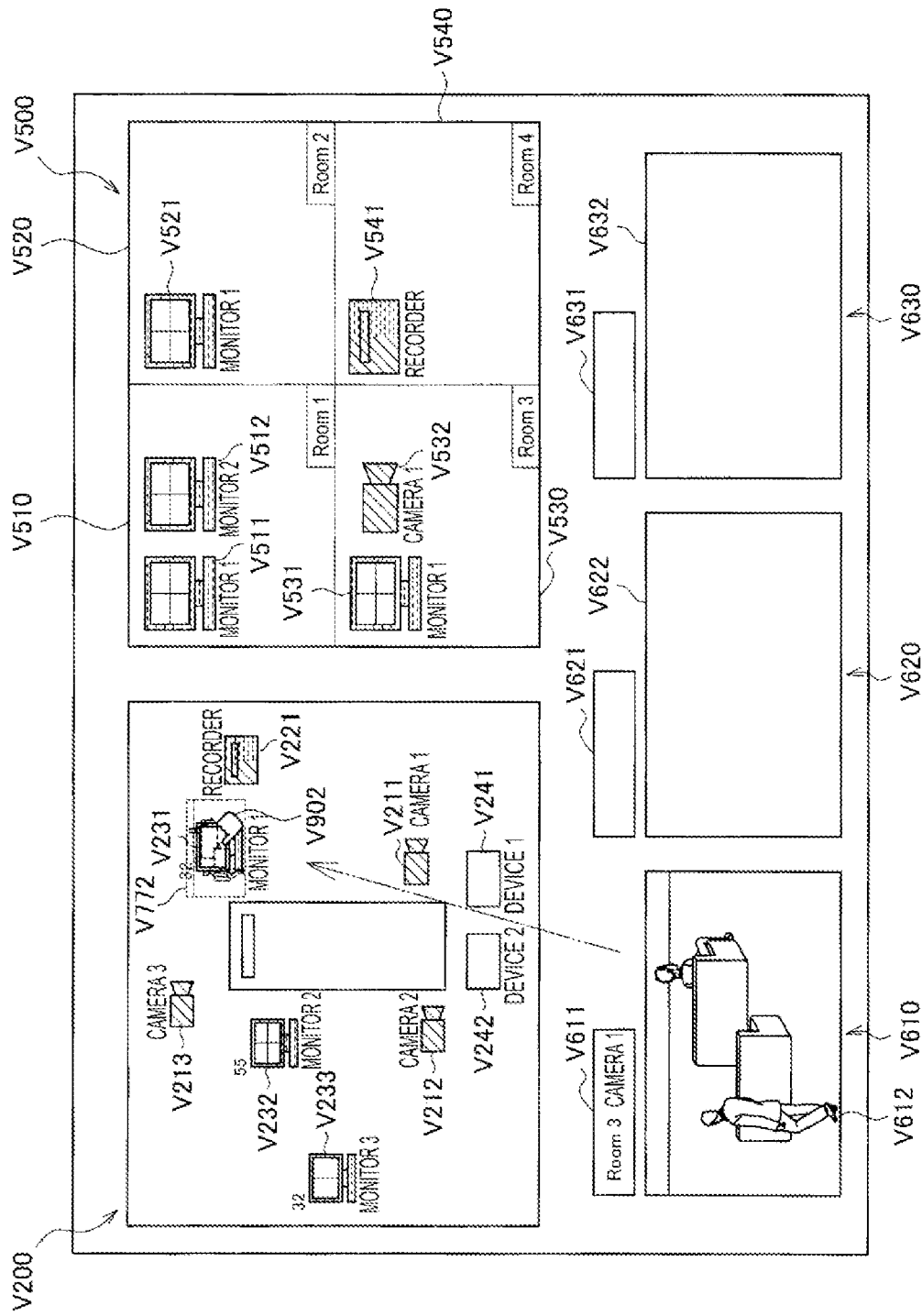
FIG. 34 is an explanatory diagram illustrating the sixth specific example according to the embodiment.

Next, FIG. 34 illustrates a state in which the mouse cursor V902 is moved in the state illustrated in FIG. 33 and drag operation is performed such that the drag icon V772 overlaps the icon V231. Here, as described above, the surgery device 2 corresponding to the icon V231 is a monitor having the function of receiving images. In this specific example, the surgery device 2 corresponding to the icon V231 may be referred to as a second device. As indicated by the icon V231, the display area of the second device is not divided. The second device is a monitor that displays an image in the entire display area.

Therefore, the device control unit 16 may generate a control signal for controlling the inter-device connection such that the first device transmits an image to the second device when the drop operation is performed in the state illustrated in FIG. 34.

Note that, the example in which an image to be transmitted from the first device is seen in advance by using the preview screen V610 and then user operation for the inter-device connection between the first device and the second device is performed, has been described above. However, the present technology is not limited thereto. For example, it is also possible to perform user operation for the inter-device connection between the first device and the second device, without seeing the image transmitted from the first device.

Figure 35:
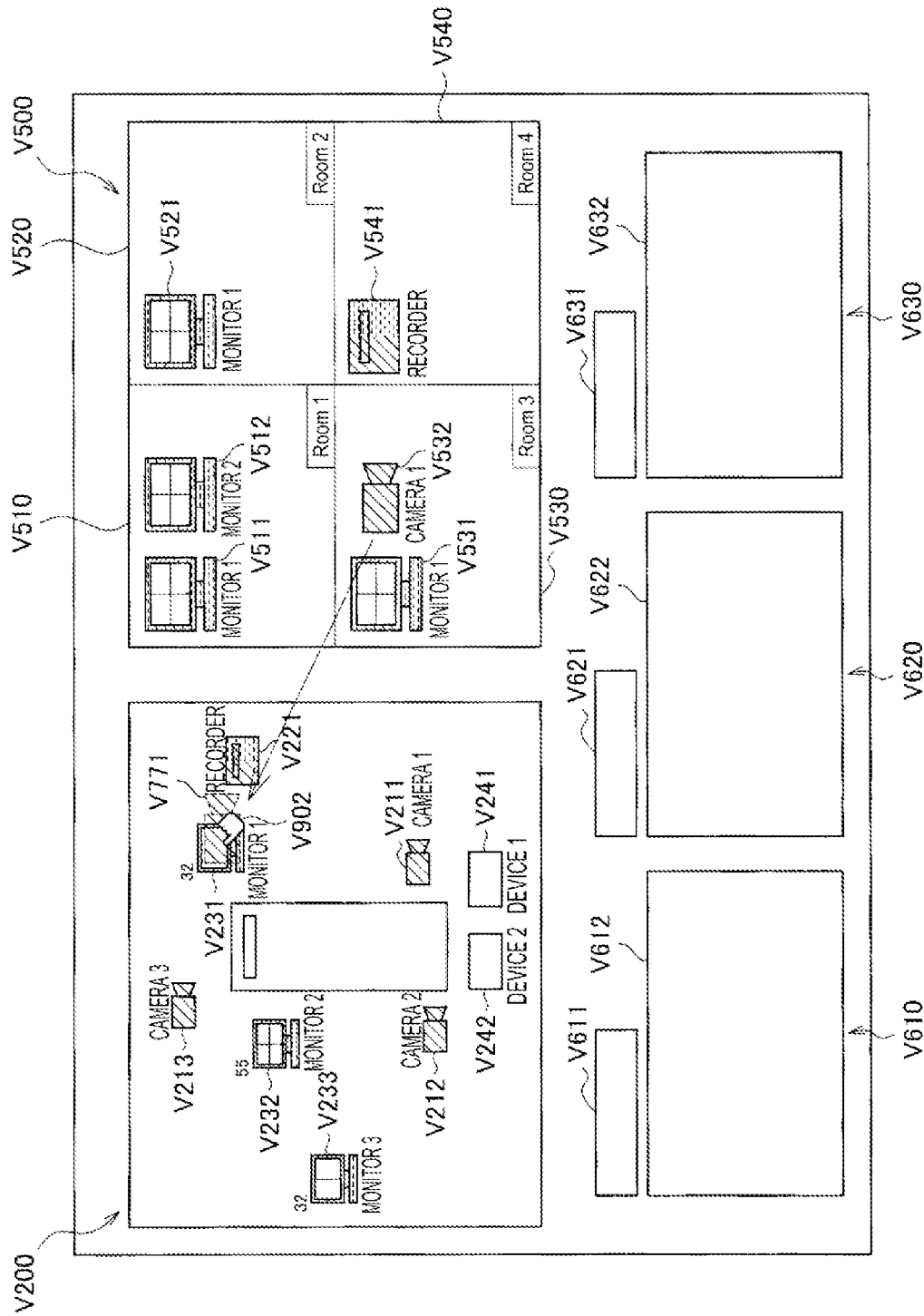
FIG. 35 is an explanatory diagram illustrating the sixth specific example according to the embodiment.

FIG. 35 illustrates a state in which the mouse cursor V902 is moved in the state illustrated in FIG. 30 and drag operation is performed such that the drag icon V771 overlaps the icon V231. The device control unit 16 may generate a control signal for controlling the inter-device connection such that the first device transmits an image to the second device when the drop operation is performed in the state illustrated in FIG. 35.

5. Hardware Configuration Example

Figure 36:
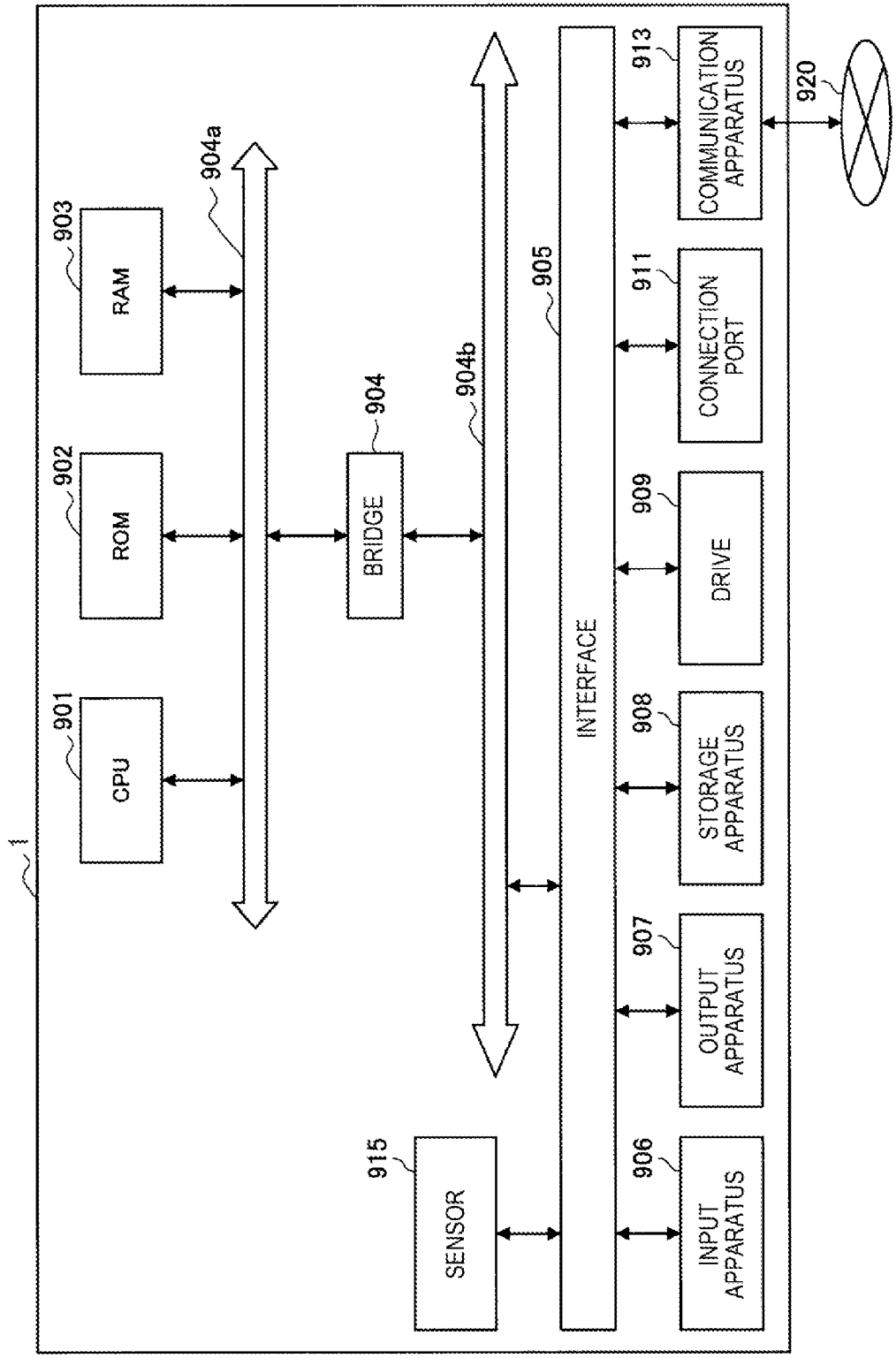
FIG. 36 is an explanatory diagram illustrating a hardware configuration example.

The embodiment of the present disclosure has been described above. Last of all, with reference to FIG. 36, a hardware configuration of the information processing device according to the embodiment of the present disclosure will be described. FIG. 36 is a block diagram illustrating an example of a hardware configuration of the information processing apparatus 1 according to the embodiment of the present disclosure. The information process performed by the information processing apparatus 1 according to the embodiment of the present disclosure is achieved by operating cooperatively software and hardware.

As illustrated in FIG. 36, the information processing apparatus 1 includes a central processing unit (CPU) 901, read only memory (ROM) 902, random access memory (RAM) 903, and a host bus 904a. In addition, the information processing apparatus 1 includes a bridge 904, an external bus 904b, an interface 905, an input apparatus 906, an output apparatus 907, a storage apparatus 908, a drive 909, a connection port 911, a communication apparatus 913, and a sensor 915. The information processing apparatus 1 may include a processing circuit such as a DSP or an ASIC instead of or in addition to the CPU 901.

The CPU 901 functions as an arithmetic processing apparatus and a control apparatus to control entire operation in the information processing apparatus 1 in accordance with various kinds of programs. The CPU 901 may be a microprocessor. The ROM 902 stores programs, arithmetic parameters, and the like used by the CPU 901. The RAM 903 transiently stores programs used when the CPU 901 is executed, various parameters that change as appropriate when executing such programs, and the like. The CPU 901 may be configured as the control unit 10, for example.

The CPU 901, the ROM 902, and the RAM 903 are connected to each other through the host bus 904a including a CPU bus and the like. The host bus 904a is connected, via the bridge 904, to the external bus 904b such as a peripheral component interconnect/interface (PCI) bus. Note that, the host bus 904a, the bridge 904, and the external bus 904b are not necessarily configured as a separate component. Their functions may be incorporated into in a single bus.

The input apparatus 906 is implemented as an apparatus allowing the user to input information, such as a mouse, a keyboard, a touchscreen, a button, a microphone, a switch, and a lever. In addition, the input apparatus 906 may be a remote controller using infrared ray or other electric waves, or may be an external connection device such as a cellular phone or a PDA that correspond to operation performed on the information processing apparatus 1, for example. Furthermore, the input apparatus 906 may include an input control circuit or the like that is configured to generate an input signal on the basis of information input by the user using the aforementioned input mechanism and output the generated input signal to the CPU 901. The user of the information processing apparatus 1 is capable of inputting various types of data to the information processing apparatus 1, or instructing the information processing apparatus 1 to perform process operation, by operating the input apparatus 906. The input apparatus 906 may be configured as the operation unit 30, for example.

The output apparatus 907 is configured as an apparatus capable of issuing a visual or auditory notification of the acquired information to the user. Examples of such an apparatus include a display apparatus such as a CRT display apparatus, a liquid crystal display apparatus, a plasma display apparatus, an EL display apparatus, or a lamp, a sound output apparatus such as a speaker or a headphone, a printer apparatus, and the like. The output apparatus 907 outputs, for example, results acquired by various processes performed by the information processing apparatus 1. Specifically, the display apparatus visually displays results acquired by various processes performed by the information processing apparatus 1 in various formats such as text, images, tables, and graphs. On the other hand, the sound output apparatus converts audio signals including reproduced sound data, audio data, and the like into analog signals and audibly outputs the analog signals. The output apparatus 907 may be configured as the display unit 40, for example.

The storage apparatus 908 is a data storage apparatus configured as an example of the storage unit of the information processing apparatus 1. For example, the storage apparatus 908 is implemented as a magnetic storage device such as an HDD, a semiconductor storage device, an optical storage device, a magneto-optical storage device, or the like. The storage apparatus 908 may include a storage medium, a recording apparatus for recording data on the storage medium, a reading apparatus for reading data from the storage medium, a deletion apparatus for deleting data recorded on the storage medium, and the like. The storage apparatus 908 stores programs and various types of data executed by the CPU 901, various types of data acquired from the outside, and the like. The storage apparatus 908 may be configured as the storage unit 50, for example.

The drive 909 is a reader/writer for a storage medium, and is incorporated in or externally attached to the information processing apparatus 1. The drive 909 reads information recorded on a removable recording medium that is mounted such as a magnetic disk, an optical disc, a magneto-optical disk, or semiconductor memory, and outputs the information to the RAM 903. In addition, the drive 909 is also capable of writing information to the removable storage medium.

The communication port 911 is an interface for connection to an external device, and is, for example, a connection port for connection to an external device capable of transmitting data via a Universal Serial Bus (USB).

The communication apparatus 913 is, for example, a communication interface configured as a communication device or the like for connection with a network 920. The communication apparatus 913 is, for example, a communication card or the like for a wired or wireless local area network (LAN), long term evolution (LTE), Bluetooth (registered trademark), or wireless USB (WUSB). In addition, the communication apparatus 913 may be a router for optical communication, a router for asymmetric digital subscriber line (ADSL), a modem for various communication, or the like. For example, the communication apparatus 913 is capable of transmitting and receiving signals and the like to and from the Internet or other communication devices, for example, in accordance with a predetermined protocol such as TCP/IP or the like. The communication apparatus 913 may be configured as the communication unit 60, for example.

The sensor 915 is various sensors such as an acceleration sensor, a gyro sensor, a geomagnetic sensor, an optical sensor, a sound sensor, a ranging sensor, or a force sensor, for example. The sensor 915 acquires information regarding the state of the information processing apparatus 1 itself such as the attitude and moving speed of the information processing apparatus 1, and acquires information regarding an environment around the information processing apparatus 1 such as brightness and noise around the information processing apparatus 1. In addition, the sensor 915 may include a GPS sensor for receiving a GPS signal and measuring the latitude, longitude, and altitude of the apparatus.

Note that, the network 920 is a wired or wireless communication path through which information is transmitted from apparatuses connected to the network 920. The network 920 may include a public network such as the Internet, a telephone network, and a satellite communication network, various local area networks (LANs) including Ethernet (registered trademark), a wide area network (WAN), and the like. In addition, the network 920 may include a dedicated network such as an internet protocol-virtual private network (IP-VPN).

The example of a hardware configuration capable of achieving the functions of the information processing apparatus 1 according to the embodiment of the present disclosure has been described above. The respective structural elements described above may be implemented using universal members, or may be implemented by hardware that is specific to the functions of each of the structural elements. Accordingly, it is possible to change a hardware configuration to be used appropriately depending on the technical level at each time of carrying out the embodiment of the present disclosure.

Note that, a computer program for implementing each of the functions of the information processing apparatus 1 according to the embodiment of the present disclosure may be created, and may be mounted in a PC or the like. Furthermore, a computer-readable recording medium on which such computer programs are stored may be provided. The recording medium is, for example, a magnetic disc, an optical disc, a magneto-optical disc, a flash memory, or the like. The computer program may be distributed, for example, through a network without using the recording medium.

6. Conclusion

As described above, according to the embodiment of the present disclosure, it is possible to control a target device more easily by causing the layout screen showing arrangement of the surgery devices to be displayed and receiving user operation for controlling a surgery device.

It should be understood by those skilled in the art that various modifications, combinations, sub-combinations and alterations may occur depending on design requirements and other factors insofar as they are within the scope of the appended claims or the equivalents thereof.

For example, the example in which a control signal for controlling inter-device connection between the first device and the second device is transmitted to the first device or the second device has been described in the above-described embodiment. However, the present technology is not limited thereto. For example, such a control signal may be transmitted to a surgery device 2 (such as a network device) that relays connection between the first device and the second device. Alternatively, the information processing apparatus 1 may have a function of relaying connection between the first device and the second device. In the information processing apparatus 1, the device control unit 16 may transmit such a control signal to a block having such a function.

In addition, it may not be necessary to chronologically execute respective steps according to the above described embodiment, in the order described in the flow charts. For example, the respective steps in the processes according to the above described embodiment may be processed in the order different from the order described in the flow charts, or may also be processed in parallel.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A surgery system including:
an information processing apparatus; and
a surgery device that is connected to the information processing apparatus,
in which the information processing apparatus includes
a display control unit configured to cause a layout screen to be displayed, the layout screen showing arrangement of the surgery device, and
a device control unit configured to generate a control signal for carrying out control regarding the surgery device.

(2)
The surgery system according to (1),
in which the device control unit generates the control signal on a basis of user operation performed on the layout screen.

(3)
The surgery system according to (1) or (2), including
a plurality of the surgery devices,
in which the information processing apparatus is connected to the plurality of surgery devices, and the layout screen shows arrangement of at least one of the plurality of surgery devices.

(4)
The surgery system according to (3), in which
the plurality of surgery devices include a first device and a second device, and
the device control unit generates the control signal for controlling connection between the first device and the second device on a basis of user operation.

(5)
The surgery system according to (4), in which
the first device has a function of transmitting an image,
the second device has a function of receiving the image, and
the device control unit generates the control signal for controlling the connection such that the first device transmits the image to the second device.

(6)
The surgery system according to (5),
in which the display control unit further causes a preview screen to be displayed on a basis of user operation, the preview screen including the image transmitted from the first device.

(7)
The surgery system according to (6),
in which the device control unit generates the control signal for controlling the connection such that the first device transmits the image to the second device on a basis of user operation performed on the preview screen and the layout screen.

(8)
The surgery system according to any one of (5) to (7), in which
the second device further has a function of simultaneously displaying a plurality of images,
the display control unit further causes a display area selection screen to be displayed for selecting a display position of the image transmitted from the first device to the second device, in the second device, and
the device control unit generates the control signal for carrying out control regarding the display position in the second device on a basis of user operation performed on the display area selection screen.

(9)
The surgery system according to any one of (3) to (8),
in which the display control unit causes a plurality of the layout screens to be displayed, each of the plurality of layout screens showing arrangement of a different surgery device among the plurality of surgery devices.

(10)
The surgery system according to (9),
in which the display control unit switches display of the plurality of layout screens on a basis of user operation.

(11)
The surgery system according to any one of (3) to (10),
in which the plurality of surgery devices include a surgery device present in a surgery room and a surgery device present outside of the surgery room.

(12)
The surgery system according to any one of (3) to (11),
in which the plurality of surgery devices include at least one of an endoscope, a microscope, a surgical field camera, or a ceiling camera.

(13)

The surgery system according to any one of (1) to (12), in which
the display control unit further causes a setting screen to be displayed for configuring a setting of the surgery device on a basis of user operation performed on the layout screen, and
the device control unit generates the control signal regarding the setting of the surgery device on a basis of user operation performed on the setting screen.

(14)

The surgery system according to any one of (1) to (13), in which the display control unit causes an icon corresponding to the surgery device to be displayed.

(15)

The surgery system according to (14),
in which the display control unit causes the icon corresponding to the surgery device to be displayed at a position in the layout screen in accordance with a position of the surgery device in a real space.

(16)

The surgery system according to (14) or (15),
in which the display control unit causes the icon corresponding to the surgery device to be displayed with an attitude in the layout screen in accordance with an attitude of the surgery device in a real space.

(17)

The surgery system according to any one of (14) to (16), in which the display control unit causes the icon corresponding to the surgery device to be displayed on a basis of a function or a state of the surgery device.

(18)

The surgery system according to (17),
in which the display control unit causes the icon corresponding to the surgery device to be displayed on a basis of whether or not the surgery device has a transmission function, or whether or not the surgery device has a reception function.

(19)

The surgery system according to any one of (17) or (18), in which the display control unit causes the icon corresponding to the surgery device to be displayed on a basis of whether or not the surgery device is in a state capable of transmitting an image that is being captured.

(20)

An information processing apparatus that is connected to a surgery device, the information processing apparatus including:
a display control unit configured to cause a layout screen to be displayed, the layout screen showing arrangement of the surgery device; and
a device control unit configured to generate a control signal for carrying out control regarding the surgery device.

(21)

An information processing method including:
causing a layout screen to be displayed, the layout screen showing arrangement of a surgery device; and
generating a control signal for carrying out control regarding the surgery device.

(22)

A medical operation system, comprising: an information processing apparatus, including processing circuitry configured to cause a map of an operating room to be displayed on a display, the map including an icon representing a device located in the operating room or accessible from the operating room, receive, via a user operation on the displayed map, designation information representing a designation of a change in at least one of an input source, an output destination, and an internal setting for the device, generate a control signal to control the device based on the designation information, and cause the generated control signal to be transmitted to the device.

(23)

The medical operation system according to (1), wherein the designation information is generated based on the user operation, which includes selecting the icon displayed on the map.

(24)

The medical operation system according to (1)-(2) wherein the processing circuitry is further configured to generate the control signal to control the device, wherein the device corresponds to the selected icon.

(25)

The medical operation system according to (1)-(3), wherein the device includes a surgical apparatus connected to the information processing apparatus; and
the map shows at least an arrangement of a plurality of icons, including a particular icon representing a location of the surgical apparatus.

(26)

The medical operation system according to (1), wherein the device includes a first device and a second device; and
the processing circuitry is further configured to generate the control signal, which controls a connection between the first device and the second device, when the designation information includes information indicating selection of a first icon representing the first device and a second icon representing the second device.

(27)

The medical operation system according to (5), wherein the first device is configured to transmit an image, the second device is configured to receive a image, and
the processing circuitry is further configured to generate the control signal to control the connections so that the first device transmits the image to the second device.

(28)

The medical operation system according to (6), wherein the processing circuitry is further configured to cause a preview screen to be displayed on the display, the preview screen includes the image transmitted by the first device.

(29)

The medical operation system according to (7), wherein the processing circuitry is further configured to generate the control signal to cause the image to be transmitted from the first device to the second device, based on the designation information generated via the user operation on the map and the preview screen.

(30)

The medical operation system according to (5), wherein the second device is further configured to simultaneously display a plurality of images, the processing circuitry is further configured to cause a display area selection screen to be displayed, the display area selection screen allowing for selection of a display position, in the second device, of the image transmitted from the first device to the second device, and the processing circuitry is further configured to generate the control signal to perform control regarding the display position in the second device, based on user input performed on the display area selection screen.

(31)

The medical operation system according to (1)-(9), wherein the processing circuitry is further configured to cause a plurality of maps to be displayed, each of the plurality of maps showing an arrangement of a different surgery device among a plurality of surgery devices.

(32)

The medical operation system according to (10), wherein the processing circuitry is further configured to switch display of the plurality of maps, based on a user input operation.

(33)

The medical operation system according to (1)-(11), wherein the device includes a first surgery device located in a surgery room and a second surgery device located outside of the surgery room.

(34)

The medical operation system according to (1)-(10), wherein the device is one of an endoscope, a microscope, a surgical field camera, and a ceiling camera.

(35)

The medical operation system according to (1)-(10), wherein the processing circuitry is further configured to causes a setting screen to be displayed, the setting screen being to configure a setting of the device based on the user operation performed on the displayed map, and the processing circuitry is further configured to generate the control signal, which controls the setting of the device, based on a user input to the setting screen.

(36)

The medical operation system according to (1)-(10), (13), and (14), wherein the processing circuitry is further configured to cause the icon corresponding to the device to be displayed at a position on the map, in accordance with a position of the device in real space.

(37)

The medical operation system according to (1)-(10) and (13)-(15), wherein the processing circuitry is further configured to cause the icon corresponding to the device to be displayed on the map with an orientation that corresponds to an orientation of the device in real space.

(38)

The medical operation system according to (1)-(10) and (13)-(16), wherein the processing circuitry is further configured to cause the icon corresponding to the device to be displayed in a manner that depends on a current function or a state of the device.

(39)

The medical operation system according to (1)-(10) and (13)-(17), wherein the processing circuitry is further configured to cause the icon corresponding to the device to be displayed based on whether or not the device has a transmission function or a reception function.

(40)

A method of controlling a device located in a medical operating room and accessible during a medical procedure in the medical operating room, the method comprising: displaying a map of the medical operating room, the map including an icon representing the device; receiving, via a user operation on the displayed map, a designation of a change in one of an input source, an output destination, and an internal setting for the device; generating a control signal to control the designated change, based on the received user operation; and causing the generated control signal to be transmitted to the device.

(41)

An image processing apparatus, comprising:
processing circuitry configured to display a map of an operating room, the map including an icon representing a device located in the operating room or useable during a medical procedure in the medical operating room, receive, via a user operation on the displayed map, a designation of a change in one of an input source, an output destination, and an internal setting for the device, and generate a control signal to control the designated change, based on the received user operation; and a transmitter configured to transmit, to the device, the generated control signal.

REFERENCE SIGNS LIST 1 information processing apparatus
2 surgery device
5 network
10 control unit
12 arrangement information control unit
14 display control unit
16 device control unit
30 operation unit
40 display unit
50 storage unit
60 communication unit
1000 surgery system

The invention claimed is:

1. A medical operation system, comprising:
an information processing apparatus, including
processing circuitry configured to
cause a map of an operating room to be displayed on a display, the map including an icon representing a first device located in the operating room or accessible from the operating room,
receive, via a user operation on the displayed map, designation information representing a designation of a change in at least one of an input source, an output destination, and an internal setting for the first device,
generate a control signal to control the first device based on the designation information, wherein the control signal controls a connection between the first device and a second device such that the first device transmits an image to the second device on condition that the designation information includes information indicating selection of a first icon representing the first device and a second icon representing the second device, wherein the first device is at least one of a ceiling camera installed in a ceiling of the operating room, a surgical field camera, and a scope for observing inside a body of a patient and the second device is a monitor for displaying images, and
cause the generated control signal to be transmitted to the first device.

2. The medical operation system according to claim 1, wherein the designation information is generated based on the user operation, which includes selecting the icon displayed on the map.

3. The medical operation system according to claim 1, wherein the processing circuitry is further configured to generate the control signal to control the first device, wherein the first device corresponds to the selected icon.

4. The medical operation system according to claim 1, wherein the first device includes a surgical apparatus connected to the information processing apparatus; and
the map shows at least an arrangement of a plurality of icons, including a particular icon representing a location of the surgical apparatus.

5. The medical operation system according to claim 1 wherein the processing circuitry is further configured to cause a preview screen to be displayed on the display, the preview screen includes the image transmitted by the first device.

6. The medical operation system according to claim 5, wherein the processing circuitry is further configured to generate the control signal to cause the image to be transmitted from the first device to the second device, based on the designation information generated via the user operation on the map and the preview screen.

7. The medical operation system according to claim 1, wherein the second device is further configured to simultaneously display a plurality of images,
the processing circuitry is further configured to cause a display area selection screen to be displayed, the display area selection screen allowing for selection of a display position, in the second device, of the image transmitted from the first device to the second device, and
the processing circuitry is further configured to generate the control signal to perform control regarding the display position in the second device, based on user input performed on the display area selection screen.

8. The medical operation system according to claim 1, wherein the processing circuitry is further configured to cause a plurality of maps to be displayed, each of the plurality of maps showing an arrangement of a different surgery device among a plurality of surgery devices.

9. The medical operation system according to claim 8, wherein the processing circuitry is further configured to switch display of the plurality of maps, based on a user input operation.

10. The medical operation system according to claim 1, wherein the first device is in a surgery room and the second device is outside of the surgery room.

11. The medical operation system according to claim 1, wherein the processing circuitry is further configured to causes a setting screen to be displayed, the setting screen being to configure a setting of the first device based on the user operation performed on the displayed map, and
the processing circuitry is further configured to generate the control signal, which controls the setting of the first device, based on a user input to the setting screen.

12. The medical operation system according to claim 1, wherein the processing circuitry is further configured to cause the icon corresponding to the first device to be displayed at a position on the map, in accordance with a position of the first device in real space.

13. The medical operation system according to claim 1, wherein the processing circuitry is further configured to cause the icon corresponding to the first device to be displayed on the map with an orientation that corresponds to an orientation of the first device in real space.

14. The medical operation system according to claim 1, wherein the processing circuitry is further configured to cause the icon corresponding to the first device to be displayed in a manner that depends on a current function or a state of the first device.

15. The medical operation system according to claim 1, wherein the processing circuitry is further configured to cause the icon corresponding to the first device to be displayed based on whether or not the first device has a transmission function or a reception function.

16. A method of controlling a first device located in a medical operating room and accessible during a medical procedure in the medical operating room, the method comprising:
displaying a map of the medical operating room, the map including an icon representing the first device;
receiving, via a user operation on the displayed map, a designation of a change in one of an input source, an output destination, and an internal setting for the first device;
generating a control signal to control the designated change, based on the received user operation, wherein the control signal controls a connection between the first device and a second device such that the first device transmits an image to the second device on condition that the designation information includes information indicating selection of a first icon representing the first device and a second icon representing the second device, wherein the first device is at least one of a ceiling camera installed in a ceiling of the medical operating room, a surgical field camera, and a scope for observing inside a body of a patient and the second device is a monitor for displaying images; and
causing the generated control signal to be transmitted to the first device.

17. An image processing apparatus, comprising:
processing circuitry configured to
display a map of an operating room, the map including an icon representing a first device located in the operating room or useable during a medical procedure in the operating room,
receive, via a user operation on the displayed map, a designation of a change in one of an input source, an output destination, and an internal setting for the first device,
generate a control signal to control the designated change, based on the received user operation, wherein the control signal controls a connection between the first device and a second device such that the first device transmits an image to the second device on condition that the designation information includes information indicating selection of a first icon representing the first device and a second icon representing the second device, wherein the first device is at least one of a ceiling camera installed in a ceiling of the operating room, a surgical field camera, and a scope for observing inside a body of a patient and the second device is a monitor for displaying images; and
a transmitter configured to transmit, to the first device, the generated control signal.

* * * * *